US007562883B2

(12) United States Patent
Livengood et al.

(10) Patent No.: US 7,562,883 B2
(45) Date of Patent: Jul. 21, 2009

(54) MODULAR PATIENT SUPPORT SYSTEM

(75) Inventors: Joseph C. Livengood, Fort Collins, CO (US); Amy L. Livengood, Fort Collins, CO (US); Barry T. Phillips, Fort Collins, CO (US); Theodore B. Ziemkowski, Loveland, CO (US)

(73) Assignee: Livengood Engineering, Inc., Fort Collins, CO (US)

( * ) Notice: Subject to any disclaimer, the term of this patent is extended or adjusted under 35 U.S.C. 154(b) by 269 days.

(21) Appl. No.: 11/329,860

(22) Filed: Jan. 10, 2006

(65) Prior Publication Data

US 2006/0163829 A1 Jul. 27, 2006

Related U.S. Application Data

(60) Provisional application No. 60/642,836, filed on Jan. 10, 2005.

(51) Int. Cl.
*A61H 3/04* (2006.01)
(52) U.S. Cl. ............... 280/87.01; 280/43.17; 280/43.24
(58) Field of Classification Search ................. 180/209; 280/79.11, 47.34, 47.35, 87.01, 33.994, 43.17, 280/43.22, 43.24; 135/67; 188/5, 6, 19
See application file for complete search history.

(56) References Cited

U.S. PATENT DOCUMENTS

| 1,793,353 | A | * | 2/1931 | Benson | 280/43 |
|---|---|---|---|---|---|
| 2,712,366 | A | * | 7/1955 | Skupas | 188/5 |
| 2,783,055 | A | | 2/1957 | Michaud | |
| 3,441,974 | A | * | 5/1969 | Dean | 16/33 |
| 3,831,960 | A | | 8/1974 | Walton | |
| 3,951,426 | A | | 4/1976 | Shaffer et al. | |
| 4,093,900 | A | * | 6/1978 | Plunkett | 318/370 |
| 4,302,025 | A | * | 11/1981 | Waddell et al. | 280/79.11 |
| 4,385,414 | A | | 5/1983 | Damico | |

(Continued)

FOREIGN PATENT DOCUMENTS

CA 2149336 8/1994

(Continued)

OTHER PUBLICATIONS

U.S. Appl. No. 12/244,623, Livengood et al.

(Continued)

*Primary Examiner*—Frank B Vanaman
(74) *Attorney, Agent, or Firm*—Sheridan Ross P.C.

(57) ABSTRACT

A patient support platform provides a solution for healthcare facilities and nursing staff to address patient and staff safety, patient mobility, patient comfort, the availability of patient information, monitoring drugs and therapy provided, and controlling health care expenses. The patient support platform preferably includes a transmission system that allows the patient and/or medical staff member to choose a stop, walk or roll mode. The transmission system preferably includes a drag wheel for applying a braking force in response to a voltage generated by a braking motor. The platform supports a plurality of devices that may be attached or associated with a patient throughout their stay at a healthcare facility. The support platform also preferably includes a mechanism for releasably attaching the support platform to another structure, such as a bed. Embodiments of the present invention include multiple non-medical uses of the platform.

30 Claims, 19 Drawing Sheets

U.S. PATENT DOCUMENTS

| | | | |
|---|---|---|---|
| 4,511,157 A | 4/1985 | Wilt | |
| 4,515,235 A | 5/1985 | Yamamoto et al. | |
| 4,832,294 A | 5/1989 | Eidem | |
| 4,970,900 A | 11/1990 | Shepherd et al. | |
| 4,998,320 A | 3/1991 | Lange | |
| 5,083,625 A | 1/1992 | Bleicher | |
| 5,083,807 A | 1/1992 | Bobb et al. | |
| 5,094,418 A | 3/1992 | McBarnes et al. | |
| 5,112,019 A | 5/1992 | Metzler et al. | |
| 5,115,539 A | 5/1992 | Lee | |
| 5,117,521 A | 6/1992 | Foster et al. | |
| 5,118,127 A | 6/1992 | Partington | |
| 5,261,682 A * | 11/1993 | Chuang | 280/42 |
| 5,306,109 A | 4/1994 | Kreuzer et al. | |
| 5,319,816 A | 6/1994 | Ruehl | |
| 5,337,992 A | 8/1994 | Pryor et al. | |
| 5,344,169 A | 9/1994 | Pryor et al. | |
| 5,358,205 A | 10/1994 | Starkey et al. | |
| 5,377,372 A | 1/1995 | Rudolf et al. | |
| 5,411,044 A | 5/1995 | Andolfi | |
| 5,509,680 A | 4/1996 | Scharf et al. | |
| 5,551,105 A | 9/1996 | Short | |
| 5,699,988 A | 12/1997 | Boettger et al. | |
| 5,704,577 A | 1/1998 | Gordon | |
| 5,735,367 A | 4/1998 | Brubaker | |
| 5,774,936 A | 7/1998 | Vetter | |
| 5,898,961 A | 5/1999 | Ambach et al. | |
| 6,000,486 A | 12/1999 | Romick et al. | |
| 6,073,285 A | 6/2000 | Ambach et al. | |
| 6,098,732 A | 8/2000 | Romick et al. | |
| 6,099,002 A | 8/2000 | Uchiyama | |
| 6,123,346 A | 9/2000 | Baldwin | |
| 6,179,260 B1 | 1/2001 | Ohanian | |
| D438,952 S | 3/2001 | Cimino et al. | |
| 6,231,016 B1 | 5/2001 | Slone | |
| D447,567 S | 9/2001 | Murphy et al. | |
| 6,286,183 B1 | 9/2001 | Stickel et al. | |
| 6,375,133 B1 | 4/2002 | Morrow | |
| 6,394,470 B1 | 5/2002 | Shirai | |
| D467,001 S | 12/2002 | Buczek et al. | |
| 6,494,469 B1 | 12/2002 | Hara et al. | |
| 6,602,227 B1 | 8/2003 | Cimino et al. | |
| 6,626,445 B2 | 9/2003 | Murphy et al. | |
| 6,708,991 B1 | 3/2004 | Ortlieb | |
| 6,865,775 B2 | 3/2005 | Ganance | |
| 6,874,800 B2 | 4/2005 | George | |
| 6,971,656 B2 | 12/2005 | Lin | |
| 7,182,350 B1 | 2/2007 | Liao | |
| 2002/0068914 A1 | 6/2002 | Ikeda | |
| 2002/0096608 A1 | 7/2002 | Cedarberg | |
| 2004/0036386 A1 | 2/2004 | Olivera | |
| 2004/0046487 A1 | 3/2004 | Olivera et al. | |
| 2004/0059303 A1 | 3/2004 | Anderson et al. | |
| 2004/0105733 A1* | 6/2004 | Hewitt | 410/66 |
| 2005/0023787 A1 | 2/2005 | Haynes | |
| 2006/0082088 A1 | 4/2006 | Webster et al. | |
| 2007/0107761 A1 | 5/2007 | Kovachi et al. | |

FOREIGN PATENT DOCUMENTS

| | | |
|---|---|---|
| GB | 2312055 | 8/1996 |
| WO | WO 00/09061 | 2/2000 |
| WO | WO 02/15837 | 2/2002 |
| WO | WO 02/24252 | 3/2002 |
| WO | WO 03/016719 | 2/2003 |
| WO | WO 03/094817 | 11/2003 |

OTHER PUBLICATIONS

Author Unknown, "Computer Carts; StyleView™ Cart with CF™", ERGOTRON, as early as Oct. 10, 2004, pp. 1-2, available at http://www.ergotron.com/3_products/carts/sview/default.asp.

International Search Report for International (PCT) Patent Application No. PCT/US06/00893, mailed Aug. 8, 2008.

Written Opinion for International (PCT) Patent Application No. PCT/US06/00893, mailed Aug. 8, 2008.

International Search Report for International (PCT) Patent Application No. PCT/US08/078609, mailed Dec. 3, 2008, pp. 1-4.

Written Opinion for International (PCT) Patent Application No. PCT/US08/078609, mailed Dec. 3, 2008, pp. 1-5.

* cited by examiner

MODULAR PATIENT SUPPORT SYSTEM

CROSS REFERENCE TO RELATED APPLICATION

The present application claims the benefit, under 35 U.S.C.§119(e), of U.S. Provisional Patent Application Ser. No. 60/642,836 filed Jan. 10, 2005, entitled "MODULAR PATIENT SUPPORT SYSTEM", the entire content of which is incorporated herein by reference in its entirety.

FIELD OF THE INVENTION

The present invention is directed to an apparatus used in the field of medicine, and more particularly, to a moveable and modular patient support system with a relatively small form factor.

BACKGROUND OF THE INVENTION

Current practice for patients in a healthcare facility involves having multiple unrelated treatment, maintenance and/or monitoring devices that are attached to the patient. These include intravenous fluids and drugs, drainage catheters, suction catheters, leg compression stockings and vital sign monitoring devices. Such devices often create a hazard for the patient both directly and indirectly. The myriad of devices may become entangled and inadvertently removed if not adequately accounted for by the patient or caregiver. This may require an invasive intervention, including surgery, in order to replace the removed device.

The number of devices generally associated with the patient require the patient to have the physical and mental ability to manage organizing or carrying the devices to ambulate even as far as the bathroom. Since patients are debilitated by the nature of their illness and medications, two staff persons are frequently required to help the patient move even short distances. One staff member must assist the patient, providing physical support, while the other manages the attached devices. The patients thus do not get out of bed and ambulate as often since the staff of the typical health facility is not able to provide this kind of support readily to all of the patients at all times.

The resulting immobility increases the patient's risk for deep venous thrombosis, pulmonary embolus and pneumonia. Additionally, mobility improves gut motility and decreases the time a patient must wait before obtaining enteral nutrition and ultimately discharge from the healthcare facility. Patients that require prolonged hospital stays or admission to skilled-nursing facilities for non-medical indications related to mobility and personnel support may be able to be discharged home sooner with a device that provides the same type of care. The cost to the healthcare system may be reduced by decreasing the stays in expensive healthcare facilities and decreasing complications that are costly both in patient morbidity and monetary value.

The patient-care staff is also at risk for injury, as they must provide physical support to the debilitated patient. Back injuries are frequent in healthcare staff as a result of the physical nature of assistance provided. Allowing the patient to rely on an ambulatory assist device will help the patient-care staff as well by keeping them out of harm's way.

Current poles that provide an intravenous ("IV") fluid and/or liquid medication delivery source are often times taken with patients when the patient moves around, such as when a patient walks in a hospital hallway. The patient typically places at least one hand on the IV pole to move the IV pole while walking. However, typical IV poles are approximately 6 to 7 feet tall, and are often unstable for providing weight support to a patient, particularly when one or more substantially full IV bags are positioned near the top of the pole. As a result, a patient is at risk of further injury by falling if the IV pole tips and/or falls over. In addition, in order to prevent tipping, conventional IV poles have widely spread wheels, which require a large amount of floor space. IV poles are completely unable to manage uneven terrain as is found outside the confines of the patient care facility, and as may be found at home or in the field for disasters or military operations.

In addition to being relatively unstable, current IV poles do not provide for the additional needs of a patient that is moving about. For example, IV poles do not include an oxygen source for assisting the patient with breathing. Current IV poles also do not include various pumps or suction devices that may be necessary for continuous operation to provide proper medical treatment to the patient. In addition, vitals monitoring equipment and communication devices are typically not present on a standard IV pole. Furthermore, even if an IV pole is adapted to include a monitoring device or pump, the IV pole tends to become even more unstable because the resulting added weight of the device typically is positioned relatively high along the pole.

In connection with patients that require assistance walking, various "walker" devices are available. A typical walker includes handrails interconnected to a stable base. However, because use of a walker usually requires both hands of the patient, a patient is typically unable to take an IV pole with them when using a walker.

A further difficulty exists when a patient needs to be moved from one room to another while in their bed. If the patient requires oxygen, an oxygen bottle must be provided, and is typically placed on the bed while moving the bed. This can create difficulties depending upon the size of the bed and the patient. Additionally, portable suction and vitals monitoring are not readily available for every patient. Accordingly, it would be advantageous to provide an apparatus that includes oxygen and other physiological support adjacent to the bed, wherein the apparatus can be attached to the bed while moving the bed. Such an apparatus would therefore also be advantageous to overcome the difficulty of maintaining monitoring equipment and/or IV fluids adjacent to the patient while moving the patient's bed. The efficiency of the staff will benefit since only a single staff member will be required to move a patient since a second staff member is not required to push the IV pole and attachments. This also prevents the need for the staff member to move the patient to a wheelchair for transfer as is currently often done in order for a single staff member to manage the transfer. Eliminating this move prevents an opportunity for a patient fall resulting in injury with only a single staff member assisting.

Patient care devices and services such as suction and oxygen are not built in to the facilities of several countries and regions. This is also true in field situations of military conflict or civilian disaster. Patients may be far from a medical facility or in the hallway of a medical facility not equipped with patient support equipment/services.

Yet a further difficulty exists in maintaining electrical power to electronic devices such as monitoring equipment, suction pumps and/or injection pumps while the patient is walking with an IV pole or walker, or while the patient is being moved in their bed or while the patient is not located next to an electrical outlet. This may occur in: 1) the operating room while needing to adjust the bed height or keep the pumps charged during a long procedure, 2) during a disaster when patients may be stationed in hallways or temporary areas, 3) during military conflict or civilian situations that require creation of field hospitals with limited generator availability, and 4) in countries or regions that do not have consistent access to power. Accordingly, an apparatus that maintains electrical power to these devices would be advantageous, as would an apparatus that provides power in case of an electrical outage or blackout.

SUMMARY OF THE INVENTION

The present invention solves the above-mentioned deficiencies by providing a mobile cart or platform that is structurally stable, and can thereby provide weight-bearing assistance to a patient without being predisposed to tipping over. In addition, the platform preferably includes one or more additional features, such as an oxygen source, power supply, injection pump, suction pump, body fluid collection devices, vital monitoring equipment, integrated IV pole and communication equipment.

In accordance with embodiments of the present invention, a modular patient support system is provided, wherein the support system typically resembles a platform, and includes a handrail interconnected to a base having three or more wheels. The support system or platform additionally may include a battery or uninterruptible power supply for serving as an emergency power supply, and/or for powering associated equipment, including the bed, while the patient is walking or being moved in a bed with the support system positioned adjacent the bed. The support platform also may include modular receptacles for receiving a variety of devices, including suction pumps, injection pumps, collection devices, monitoring equipment, and communication devices. An electrical wiring network may be provided such that the modular devices interconnected to the support platform receive electrical power directly at the modular receptacles, thereby minimizing the presence of numerous power cords. Such additional equipment is powered by the uninterruptible power supply when the support platform is disengaged from a stationary power supply, such as an electrical wall outlet.

In accordance with other embodiments of the present invention, the support platform may include an on-board communication system to send monitoring information or other data to a nurses' PDA, central station or alarm system. The communication system may include wireless communication to transmit a patient's vitals, equipment status, fluid volumes, therapy status and location for providing information while a patient is using the support platform as a walking aid. An interface may be provided for the healthcare providers to be able to access and interact with the facility's electronic medical record system.

In accordance with other embodiments of the present invention, the support platform may include a checkpoint validation system to ensure the correct therapy is administered to the correct patient. This may involve identification of the patient, platform and therapy (such as intravenous fluids, medications or equipment) with devices such as barcodes, radiofrequency identifiers or other similar technology to match and track all therapy provided.

In accordance with other embodiments of the present invention, the support system also may also include an on-board oxygen supply and associated tubing. Additionally, the support platform may include an IV fluids/medication support assembly, such as an IV pole with an attachment hook.

The support platform may be configured in a variety of ways, to include a cabinet or other enclosure for holding items such as a urine collection bag, body fluid collection bag and suction canister. The configuration of the support platform also may include specially sized compartments for bottles or cups, and may include other built-in features such as a tray, radio, television, phone, computer or other communication device, wherein some of these devices may also be interconnected to the support platform's power supply.

In a separate aspect of the invention, an attachment device is provided for detachably attaching the support platform to another structure, such as the patient's bed. The attachment device may include an attachment adapter capable of being interconnected to a variety of bed frame structures, regardless of whether the framing includes square or round rails or posts. The attachment device not only secures the support platform to the bed so that it is not moved when accidentally bumped, but it also enables the support platform to be moved with the bed without the need for a separate attendant to move the support platform. In at least one embodiment, a plurality of bed hooks are used to enable the platform to grasp another object, such as a bed, when the bed is raised to impinge upon the underside of the bed hooks.

In a separate aspect of the invention, the support platform includes an umbilical cord having a common plug for interconnecting a plurality of systems to a single outlet, such as a wall outlet. The umbilical cord may support a variety of systems, including electrical power, oxygen, suction, and/or a communication connection.

In accordance with embodiments of the present invention, a locking brake may optionally be provided to limit movement of the platform if the brake is engaged. The brake may have mechanisms that engage it actively and/or passively. This may include a 'kill-switch' device that detects separation of the patient from the platform in situations that may result in patient injury if such event occurs.

In accordance with embodiments of the present invention, a transmission system may be provided to allow a user or other person to place the platform in one of a plurality of possible translation modes. In at least one embodiment, the transmission system includes stop, walk and roll modes. The stop mode engages a brake to contact the underlying surface, thereby substantially preventing the platform from rolling. In addition, in at least one embodiment, both a drag wheel and a brake are in contact with the floor when the platform is set in the stop mode. The walk mode includes raising the brake, if present, and engaging a drag wheel to contact the floor. Although not prevented from moving, the walk mode helps prevent undesirable fast movement of the platform. In one embodiment, the drag wheel may comprise a wheel that is preset to turn at a very slow rate. Alternatively, in at least one embodiment the drag wheel may be interconnected to a braking motor, operated as a generator powered by the drag wheel, that applies a resistive force or an increased resistive force to the drag wheel when velocities increase above an undesirable level. For example, if a patient is standing adjacent the support platform and starts to slip while holding the handle of the platform, the braking motor will apply a resistive force to the drag wheel, thereby preventing the support platform from moving away from the patient and/or moving away from the patient at a high rate of speed. A variety of motor braking circuit configurations and braking functions are available for controlling the resistive force applied to the drag wheel using the braking motor. For example, a motor braking circuit may provide different resistive loads to the braking motor based on the velocity of the braking motor. In addition, the motor braking circuit does not require any source of power other than the power generated as a result of the rotation of the braking motor by the drag wheel. In the roll mode the transmission disengages both the brake and the drag wheel, such that the platform may be easily rolled. This setting is anticipated for use, for example, when an attendant is moving the platform.

Thus, in accordance with at least one embodiment of the present invention, a personal support platform for traversing an underlying surface is provided, the platform comprising a frame and a plurality of wheels interconnected to the frame. In addition, the platform comprises a transmission system interconnected to the frame, the transmission system providing a number of user selectable modes, the user selectable modes comprising at least a stop mode, a walk mode and a roll mode. Finally, in at least one embodiment, the platform further comprises a means for selectively choosing one of the stop, walk and roll modes by a user from a standing position adjacent the frame.

In a separate aspect of the invention, a transmission system of the platform comprises a drag wheel that is selectively moveable from a first raised position in the roll mode to a second lowered position in the walk mode, and wherein the drag wheel is for contacting the underlying surface when in the second lowered position. In addition, in accordance with at least one embodiment, the transmission system comprises a cam interconnected to the frame and the drag wheel, wherein the cam is rotatably movable to raise and lower the drag wheel from the first raised position in the roll mode to the second lowered position in the walk mode. The transmission system may also further comprise an automatic brake interconnected to the drag wheel, wherein the automatic brake comprises a braking motor driven by the drag wheel and circuitry, wherein the circuitry provides a resistive load to the braking motor to apply a braking force on the drag wheel. In addition, in at least one embodiment, the resistive load comprises a number of load ranges, wherein a first load range provides a first resistive load within a first velocity range for the braking motor, and wherein a second load range provides a second resistive load within a second velocity range for the braking motor. Also, the second velocity range may be automatically selected once a threshold velocity of the braking motor is reached.

In a separate aspect of the invention, a transmission system of the platform may comprise a brake interconnected to the frame, wherein the brake is selectively moveable from a first raised position in the walk and roll modes to a second lowered position in the stop mode, and wherein the brake is for contacting the underlying surface when in the second position. In at least one embodiment, the brake comprises a stopper frictionally engaging the underlying surface. In yet a separate aspect of the invention, the platform may comprise a cam having a first channel interconnected to the brake. In at least one embodiment of the invention, the cam comprises a second channel interconnected to a drag wheel. In accordance with at least one embodiment of the invention, the first channel comprises a first ramp for raising and lowering a first post interconnecting the drag wheel to the cam, and wherein the second channel comprises a second ramp for raising and lowering a second post interconnecting the stopper to the cam.

In a separate aspect of the invention, a means for selectively choosing the mode of the transmission system comprises a first handle at a rear portion of the frame, wherein the handle is selectively adjusting a setting of the transmission system. In at least one embodiment, the transmission system may further comprise a second handle at a front portion of the frame, wherein the second handle can also be used for selectively adjusting a setting of the transmission system.

In a separate aspect of the invention, the platform comprises at least one grasping mechanism for interconnecting the frame to another structure. In at least one embodiment of the invention, the grasping mechanism comprises a rotatable gripper arm that engages the other structure. In addition, in at least one embodiment, the rotatable gripper arm rotates about a first axis in a direction away from the frame, and rotates about a second axis to grasp the other structure, wherein the second axis is transverse to the first axis.

It is a further aspect of the present invention to utilize a variety of devices to provide functionality to a personal support platform. Accordingly, in at least one embodiment of the present invention, a personal support platform for traversing an underlying surface is provided, comprising a frame and means for rotating interconnected to said frame and contacting the underlying surface. The platform further comprises means for frictionally engaging the underlying surface and interconnected to said frame; and means for variably controlling a resistance provided by said means for frictionally engaging. In at least one embodiment of the invention, the means for rotating comprises a plurality of wheels. In addition, it in at least one embodiment of the invention the means for frictionally engaging comprises a drag wheel. In accordance with at least one embodiment of the invention, the means for frictionally engaging is interconnected to a means for adjusting a position of said means for frictionally engaging, wherein said means for adjusting may alter a position of said means for frictionally engaging from a first position in contact with the underlying surface to second position wherein said means for frictionally engaging does not contact the underlying surface. In at least one embodiment of the invention, the means for adjusting comprises a selectably positionable cam for raising and lowering said means for frictionally engaging. In addition, in at least one embodiment of the invention the means for variably controlling a resistance comprises a passive braking motor. In a separate aspect of the invention, the passive braking motor comprises a motor braking circuit interconnected to the passive braking motor. In at least one embodiment, the braking circuit includes a first circuit stage, including a switching mechanism, wherein an activation voltage for the first circuit stage is defined. The circuit also includes, a load resistor, wherein when the passive braking motor produces an amount of power sufficient to produce a voltage at the switching mechanism that is equal to or greater than the activation voltage and above a current is allowed to pass through the load resistor.

As noted above, embodiments of the present invention may comprise a braking system. Thus, in accordance with at least one embodiment of the invention, a passive variable braking system is provided, comprising:

a motor;

a motor braking circuit interconnected to the motor, including:

a first circuit stage, including:

a switching mechanism, wherein an activation voltage for the first circuit stage is defined; and a load resistor, wherein when the motor produces an amount of power sufficient to produce a voltage at the switching mechanism that is equal to or greater than the activation voltage and above a current is allowed to pass through the load resistor.

In a separate aspect of the invention, the motor braking circuit of the passive variable braking system further comprises:

a second circuit stage in parallel with the first circuit stage, the second circuit stage including:

a switching mechanism, wherein an activation voltage for the second stage is defined;

a load resistor, wherein when the motor produces an amount of power sufficient to produce a voltage at the switching mechanism that is equal to or greater than the activation voltage and above a current is allowed to pass through the load resistor, wherein the activation voltage for the second stage is greater than the activation voltage for the first stage, and wherein when the activation voltage for the second stage is met or exceeded a current continues to be allowed to pass through the load resistor of the first circuit stage.

In yet a separate aspect of the invention, the passive variable braking system further comprises:

a switch, wherein the first and second circuit stages comprise a number of load resistors, wherein the switch is operable to select one of each of the load resistors included in the first and second circuit stages to provide a selected resistance at the motor.

In a separate aspect of the invention, the motor braking circuit of the passive variable braking system further comprises:

a second circuit stage in parallel with the first circuit stage, the second circuit stage, including:

a switching mechanism, wherein an activation voltage for the second stage is defined; and a load resistor, wherein when the motor produces an amount of power sufficient to produce a voltage at the switching mechanism that is equal to or greater than the activation voltage and above a current is allowed to pass through the load resistor, and wherein the activation voltage for the second stage has a polarity that is opposite the activation voltage for the first stage.

In a separate aspect of the invention, the switching mechanism of the passive variable braking system comprises a zener diode.

In a separate aspect of the invention, the switching mechanism of the passive variable braking system comprises a pair of voltage dividing resistors and a transistor, wherein a voltage divided by the pair of resistors is provided to a gate of the transistor.

In yet a separate aspect of the invention, the switching mechanism of the passive variable braking system comprises a resistor interconnected to a Silicon Controlled Rectifier.

In yet a separate aspect of the invention, the passive variable braking system further comprises a drag wheel interconnected to the motor, wherein the motor is driven by the drive wheel. In yet a separate aspect of the invention, the drive wheel is interconnected to the motor by a gearbox.

In still yet a separate aspect of the invention, the switching mechanisms of the passive variable braking system of the first and second circuit stages each comprise a zener diode, and wherein the first and second stages each additionally include a blocking diode.

It is a separate aspect of the present invention to provide a method of using a support platform that comprises one or more features of the device described herein. Accordingly, a method of using a personal support platform is provided, the method comprising selecting a transmission mode for a transmission system operably associated with the personal support platform, wherein the transmission system provides a number of user selectable transmission modes, and wherein the user selectable transmission modes comprise at least a stop mode, a walk mode and a roll mode. In accordance with at least one embodiment of the present invention, the personal support platform for use includes a frame, a plurality of wheels interconnected to the frame, and a transmission control device operably interconnected to the transmission system, the transmission control device adapted for allowing a user to selectively choose one of the stop, walk and roll modes. In the method of use, the selecting step comprises manipulating the transmission control device to one of the stop, walk and roll modes. In addition, in at least one embodiment, the manipulating step comprises moving a control bar operably interconnected to the frame and a cam, wherein the control bar controls positions of a drag wheel and a brake that are operably interconnected with the cam. In a separate aspect of the invention, in at least one embodiment the method of use also comprises inducing a braking force on the drag wheel by at least temporarily increasing a velocity of the frame, wherein the resistive force is imposed by an automatic brake interconnected to the drag wheel, wherein the automatic brake comprises a braking motor driven by the drag wheel and circuitry, and wherein the circuitry provides a resistive load to the braking motor to apply a braking force on the drag wheel. In addition, in at least one embodiment, the method also comprises releasably connecting the platform to another structure using at least one grasping mechanism interconnected to the frame, and may further comprise impinging at least a portion of the other structure against the rotatable gripper arm.

In accordance with embodiments of the present invention, a method of using a personal support platform is provided comprising: providing a drag wheel interconnected to the platform, the drag wheel for contacting a surface under the platform; positioning the drag wheel to contact the surface under the platform; and applying a braking to the platform through the drag wheel by applying at least a first braking resistance to the drag wheel for at least a first velocity range of the drag wheel. In at least one aspect of the invention, the method may further comprise providing at least a second braking resistance to the drag wheel for at least a second velocity range of the drag wheel. In another aspect of the invention, the second velocity range is automatically selected once a threshold velocity of a braking motor is reached. In accordance with at least one embodiment of the invention, the positioning step of the drag wheel further comprises manipulating a transmission control device to lower the drag wheel in contact with the surface under the platform. The method may further comprise engaging a stopper to contact the surface underlying the platform. In addition, the method may comprise releasably connecting the platform to another structure using at least one grasping mechanism interconnected to the platform. In accordance with at least one embodiment of the invention, the step of releasably connecting the platform to another structure may also comprise impinging at least a portion of the other structure against a portion of the grasping mechanism.

Various embodiments of the present invention are set forth in the attached figures and in the detailed description of the invention as provided herein and as embodied by the claims. It should be understood, however, that this Summary of the Invention may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

DETAILED DESCRIPTION OF THE INVENTION

In accordance with embodiments of the present invention, a platform is provided that has application for use in a variety of fields, one of which is in the field of health care. Various embodiments of the platform may include an ergonomic structure suited for a patient to use the platform as a walking aid. In addition, embodiments of the invention may also comprise structure for accommodating on-board health monitoring and/or treatment equipment. These and other features are described in detail below.

Figure 1:
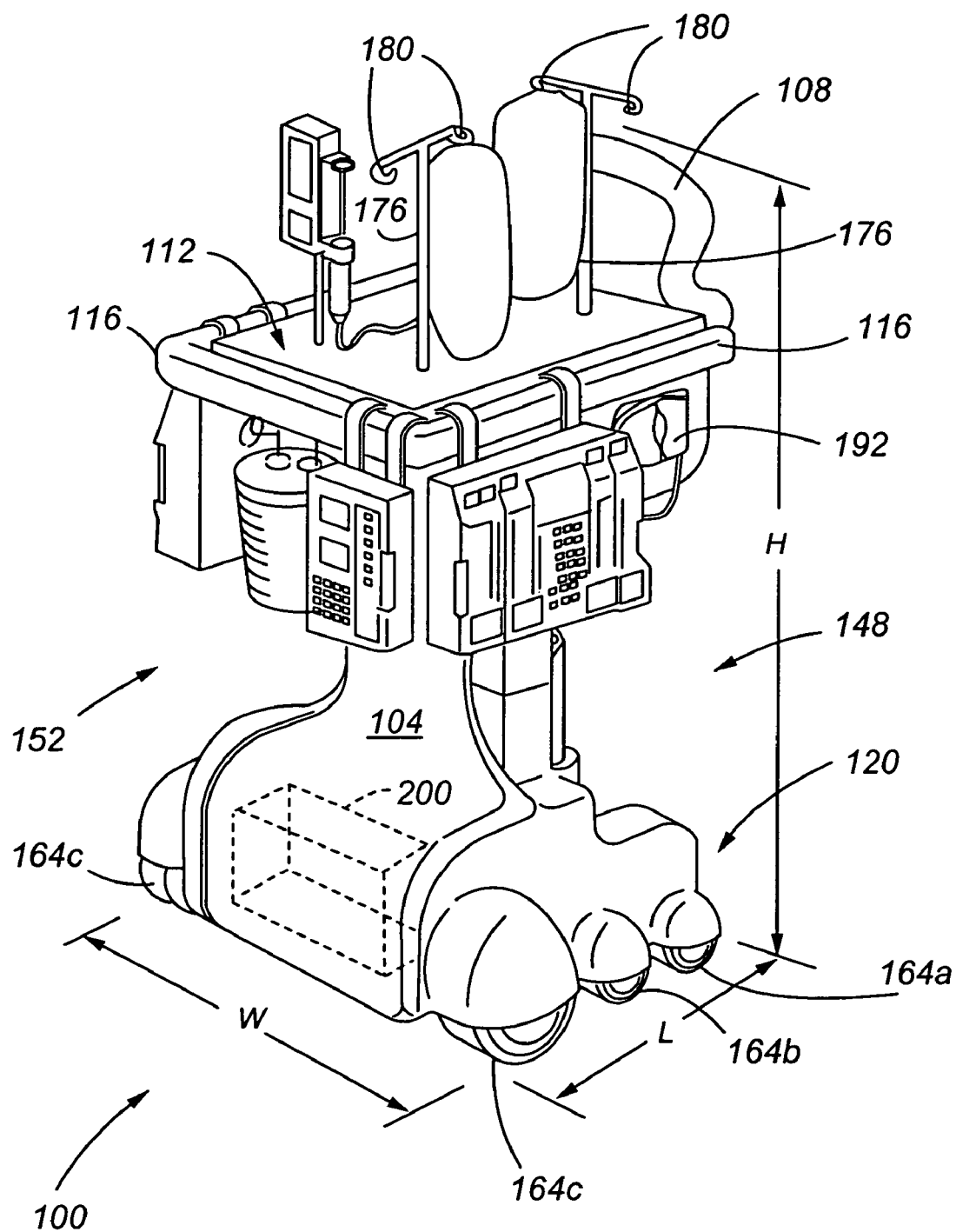
FIG. 1 is a perspective view of an apparatus in accordance with embodiments of the present invention.

Referring now to FIG. 1, an apparatus constructed in accordance with an embodiment of the present invention is generally identified by reference numeral 100. Support platform 100 includes a chassis, support frame or body 104 having a platform handle 108 located at or near a top 112 of the platform 100. The platform 100 also includes a perimeter rail 116 at its top 112, wherein the perimeter rail 116 is adapted for receiving a variety of health monitoring, treatment, or maintenance devices, such as equipment currently available for these purposes. The platform 100 further includes a base 120 described in further detail below.

Figure 2:
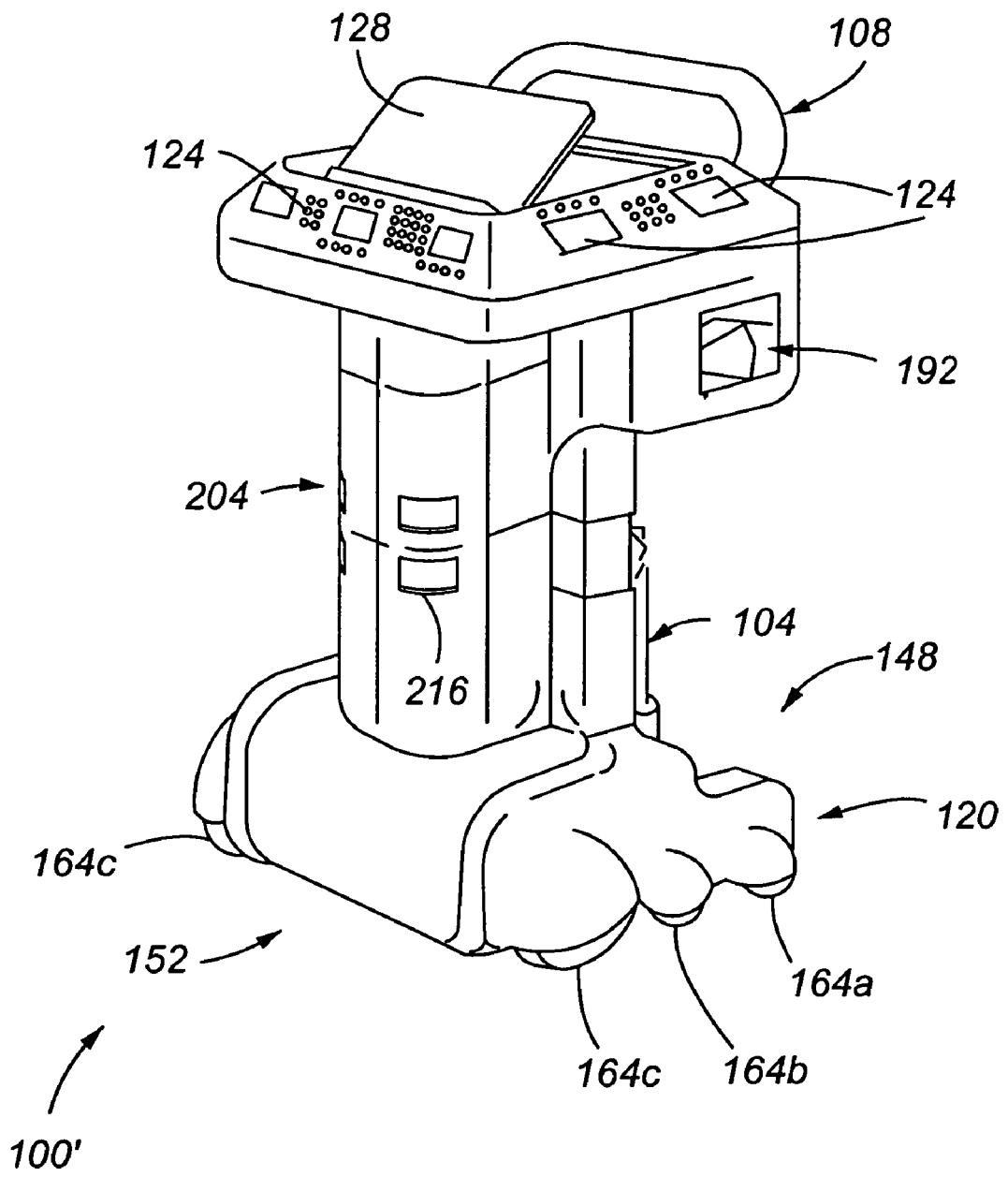
FIG. 2 is a perspective view of another apparatus in accordance with embodiments of the present invention.

Referring now to FIG. 2, an embodiment in accordance with the present invention is depicted wherein support platform 100' internalizes at least one of a number of ancillary devices that may be associated with the platform, and more preferably, the platform 100' internalizes a plurality of such ancillary devices. Accordingly, the support platform 100' preferably includes one or more modular receptacles 124 for items such as suction pumps, IV pumps, infusion pumps, and/or monitoring equipment. In addition, the support platform 100' may further included a receptacle or port for a personal computer 128. The receptacles replace the current pump technology and incorporate the devices into the platform to reduce its profile, overall weight and simplify the total set of devices attached to the patient.

Figure 3:
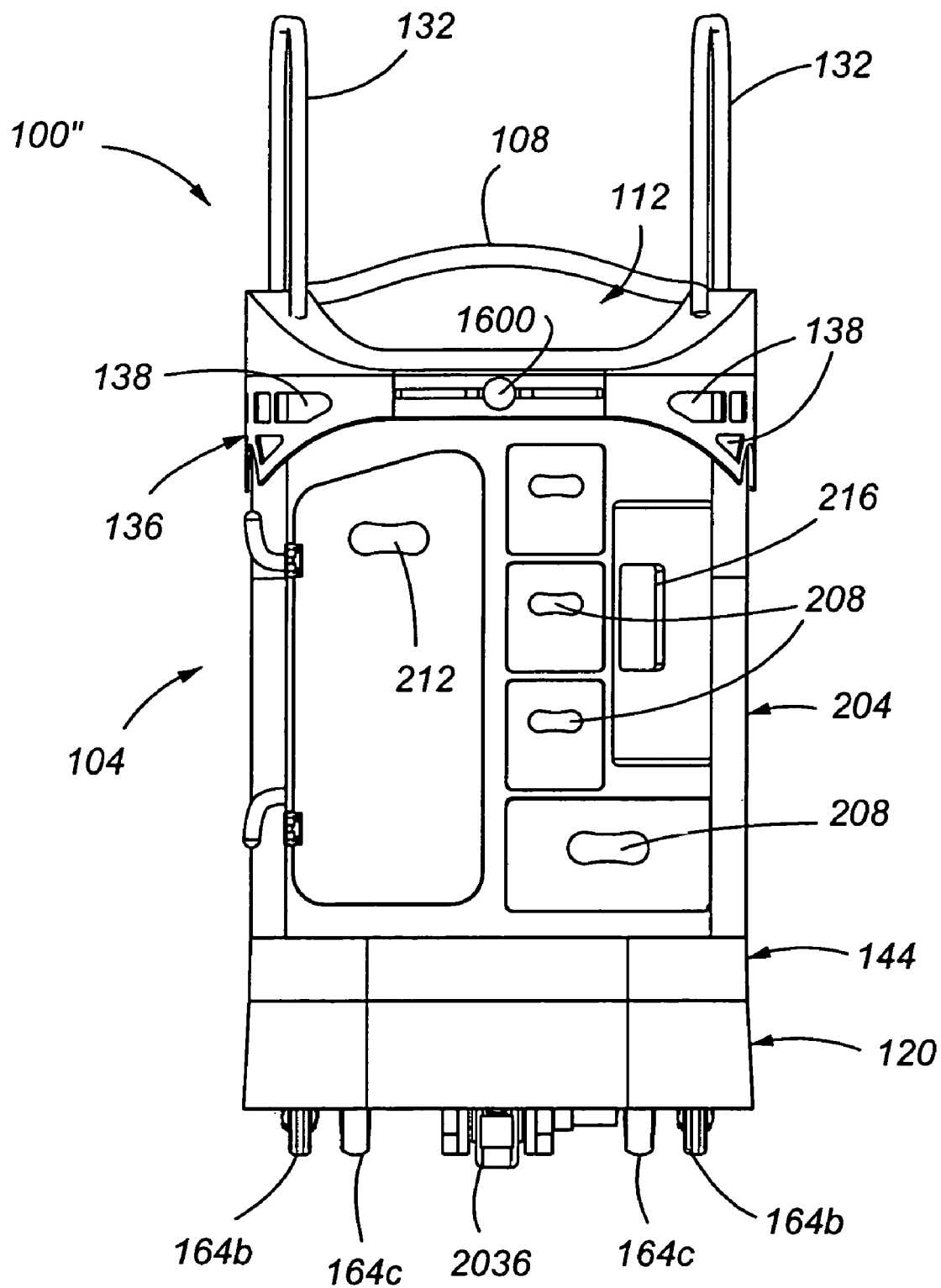
FIG. 3 is a front elevation view of yet another apparatus in accordance with embodiments of the present invention.
Figure 4:
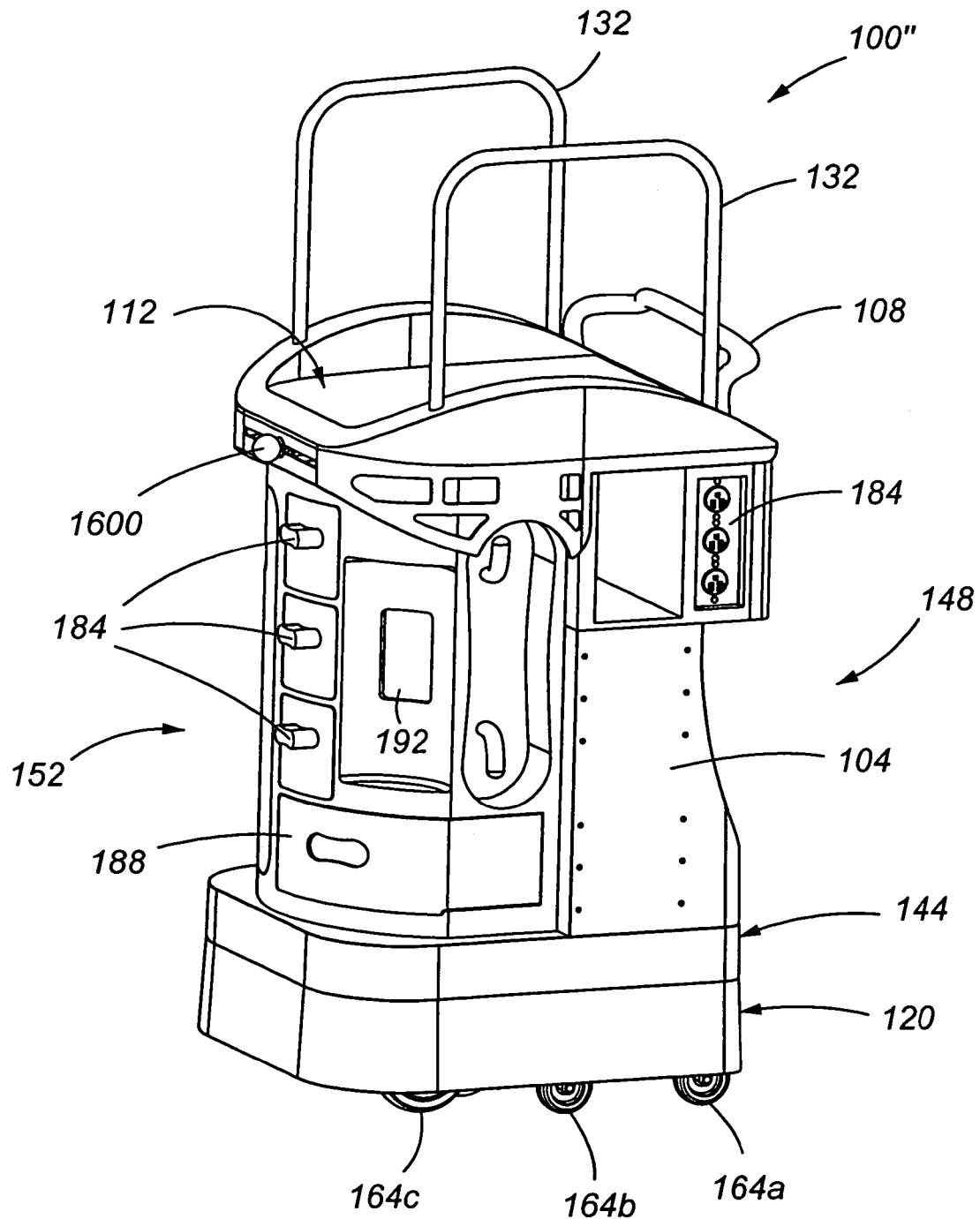
FIG. 4 is a front perspective view of the platform shown in FIG. 3.
Figure 5:
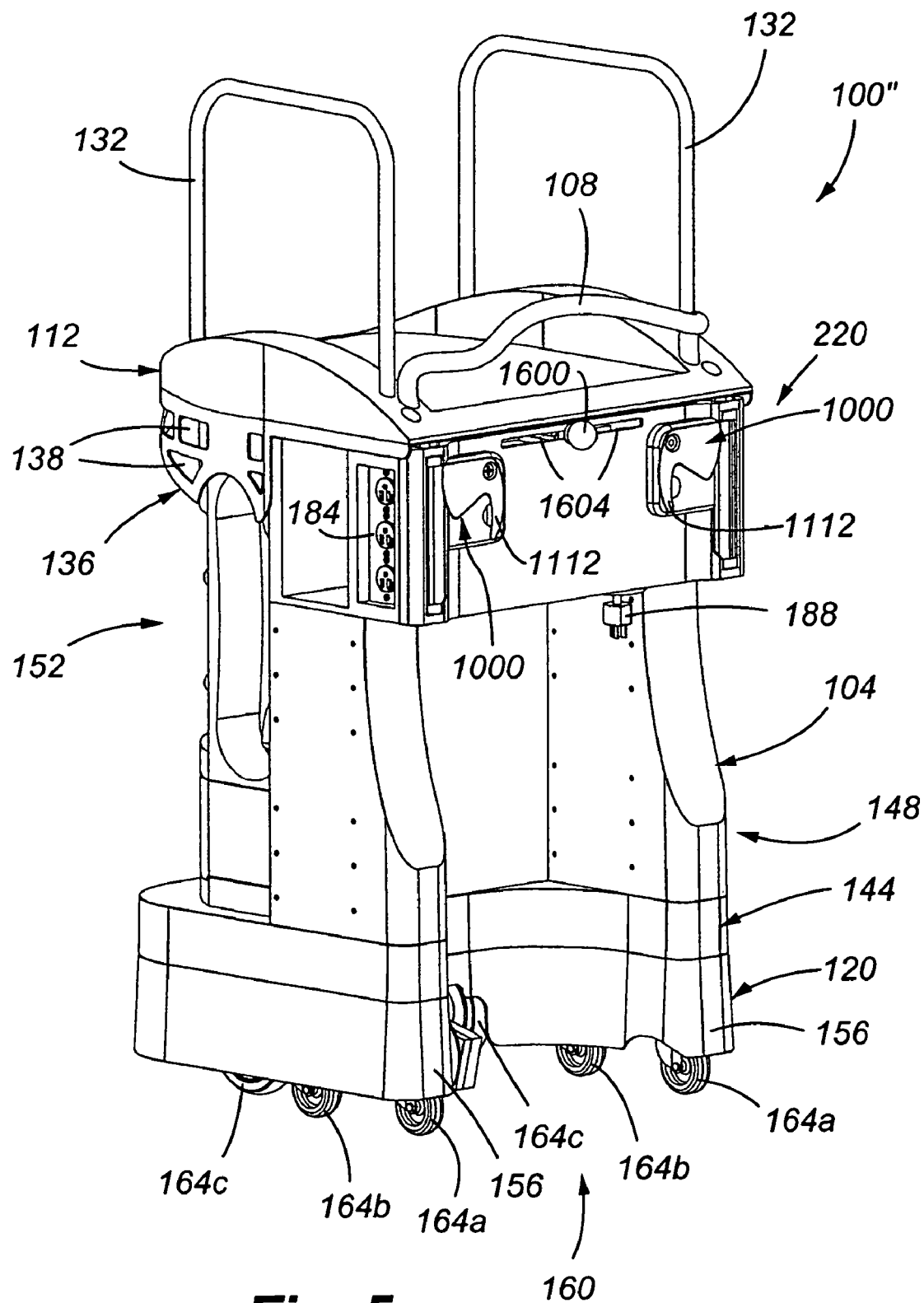
FIG. 5 is a rear perspective view of the platform shown in FIG. 3.

Referring now to FIGS. 3-5, an embodiment in accordance with the present invention is depicted as support platform 100". Support platform 100" features a substantially open top 112 with a pair of elevated rails 132. In accordance with embodiments of the present invention, the perimeter of the top 112 includes a skirt 136 with one or more openings 138 for receiving hooks or other connecting hardware to attach a variety of health monitoring, maintenance and/or treatment devices.

Thus, embodiments of the present invention may comprise a substantially open configuration, as shown in FIG. 1 as support platform 100, or a modular and substantially internalized configuration, as shown in FIG. 2 as support platform 100', or an alternate configuration having interior cabinet space with a substantially open top 112, as shown in FIGS. 3-5 as support platform 100", or other configurations, all of which are encompassed by the present invention and this description. Although support platforms 100, 100', 100" may have a variety of different features, they may also share similar structure and have various combinations of features. The following text and associated referenced drawings describe features that may be used individually or in combination for various embodiments of the present invention.

Figure 6:
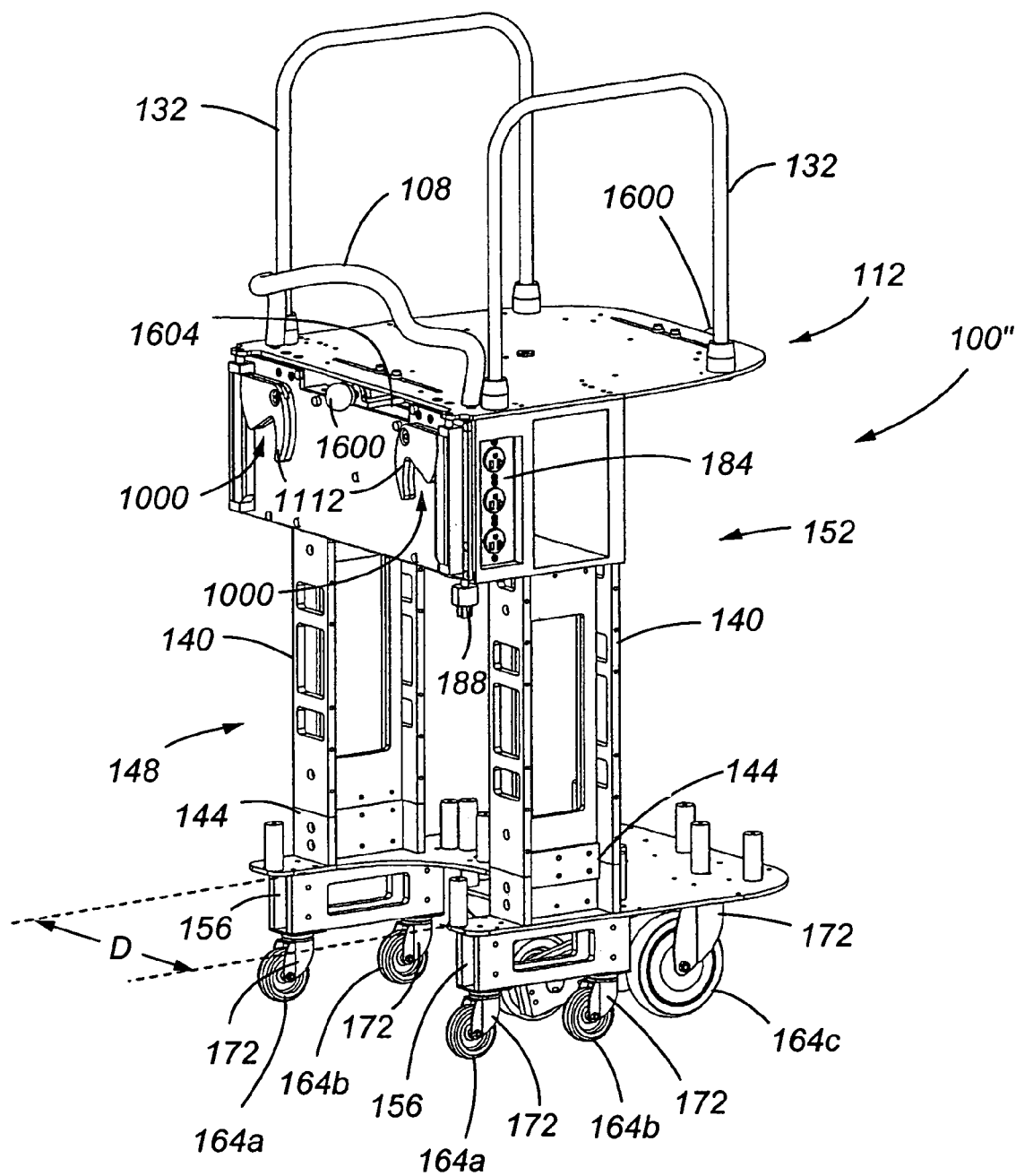
FIG. 6 is a rear perspective view of the platform shown in FIG. 3, wherein the platform is shown without a surface layer.

Referring to FIGS. 1-3, support platform 100, 100', 100" include a body 104 having a height H. Height H is preferably a sufficient height for allowing a patient to stand and grasp platform handle 108 at the top 112 of the support platform 100, 100', 100" to aid the patient in support and/or balance while walking or standing. Height H is preferably adjustable, thereby allowing the support platform 100, 100', 100" to be modified to accommodate the height of the patient. Since patients vary from small children to large adults, the height H of the support platform 100, 100', 100" pertains to a functional aspect of the invention. Accordingly, the body 104 may include an adjustable or telescoping means for selectively varying the height H of body 104. The telescoping means may include one or more adjustable columns, and/or otherwise include interchangeable columns 140, such as those shown in FIG. 6, wherein FIG. 6 depicts a skeletonized view support platform 100". In accordance with embodiments of the present invention, the columns 140 allow for adjustment of the height of the platform. Further, and in accordance with other embodiments of the present invention, one or more spacers 144 may also be incorporated into the body 104 of the support platform 100, 100', 100", wherein each spacer 144 serves to add additional height. In at least one embodiment, the spacer 144 comprises a supplemental height member having a thickness of between about 1-6 inches, and more preferably between about 2 to 4 inches. For the various embodiments of the present invention, the height H of the support platform 100, 100', 100" is between about 24 and 48 inches tall, and more preferably, between about 30 and 40 inches tall. However, other heights for short, tall and physically challenged individuals, and/or for platforms having other uses other than in the health care field are all within the scope of the present invention.

As noted above, the frame 104 of support platform 100, 100', 100" preferably includes a base 120, wherein the base has a stable configuration for supporting both the items on the support platform 100, 100', 100", as well as being able to support the added weight of a patient leaning on the platform handle 108. Accordingly, the base 120 is relatively large, but not too large so as to be clumsy to manipulate. For the embodiments shown in FIGS. 1-5, the base 120 is substantially rectangular in shape, with a width W and a length L. For a rectangular base 120, the width W is preferably between about 16 to 28 inches wide, and more preferably between about 18 to 24 inches wide. The length L is preferably between about 16 to 28 inches long, and more preferably between about 18 to 24 inches long. However, it is to be understood that the base 120 may be a variety of shapes and configurations. For example, the base 120 may have a footprint that is substantially circular or hexagonal in shape.

As best seen in FIG. 6, the base 120 has a rear portion 148 and a front portion 152. Rear portion 148 preferably includes spaced apart base beams 156. The base beams 156 are preferably spaced apart to provide a preferential unobstructed area or opening 160 for the patient to place their feet while holding the platform handle 108 and walking. Accordingly, the base beams 156 are preferably spaced apart a distance D, where distance D preferably varies between about 10 inches and 24 inches, and more preferably between about 14 inches and 20 inches. Providing a properly sized spaced apart distance D provides for increased safety for the patient so that the patient does not trip when walking with the support platform 100, 100', 100".

In accordance with other embodiments of the invention, the base 120 may not be directional, or alternatively, the direction may be determined by the user to maximize the benefit of the wheel design to their health and expected use. For example, the wheel configuration may benefit weaker patients to overcome small obstacles when the base is oriented in a first direction. Conversely, healthier patients that expect to travel farther and faster may find that they have better control of the invention by changing the direction of the platform by 180°.

The base 120 preferably includes a plurality of casters or wheels 164. More preferably, the base 120 includes at least three wheels set in a triangular orientation, and more preferably yet, at least four, five or six wheels spaced apart in various configurations along the bottom of the footprint of base 120. As seen in FIG. 6, and in accordance with embodiments of the present invention, at least some of the wheels 164 preferably include a swivel connector 172 between the wheel 164 and the base 120 of support platform 100, 100', 100". For example, the middle pair of wheels 164b and the rear pair of wheels 164a (interconnected by the base beams 156) may include swivel connectors 172, while the orientation of the front wheels 164c may be fixed. Alternatively, all wheels 164 may have a swivel connector 172 between the wheel 164 and the base 120.

Figure 7:
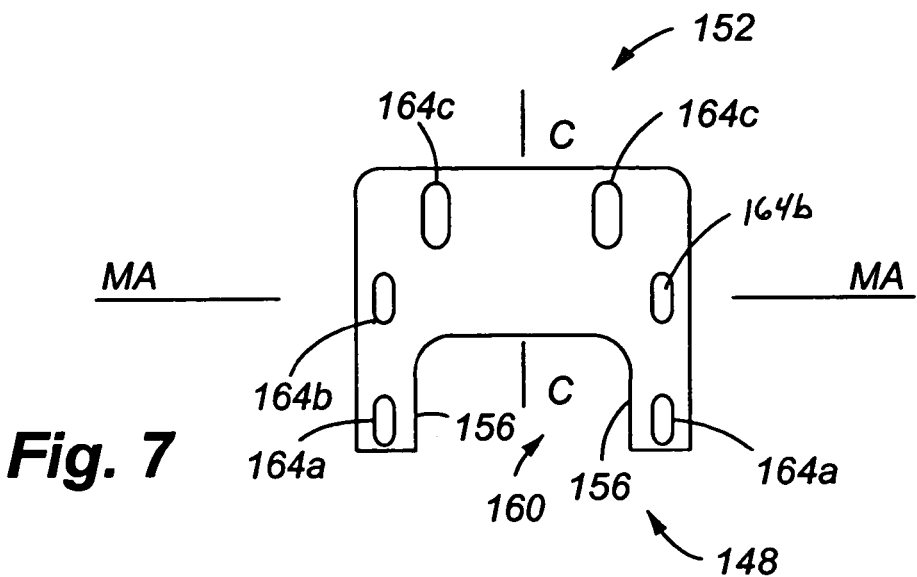
FIG. 7 is a bottom view of the wheels of the platform shown in FIG. 3.

Referring now to FIG. 7, the underside of base 120 of a first preferred embodiment is illustrated. Base 120 is shown having a substantially C-shaped overall footprint when viewed from a side of the support platform 100, 100', 100". In accordance with at least one embodiment of the present invention, the base 120 comprises six wheels 164 that provide a means for rotating that is interconnected to the frame and contacting the underlying surface, such as a floor surface. A first pair of wheels 164a is preferably positioned under beams 156 at the rear portion 148 of the base 120, such that one wheel 164a is under a left base beam 156 and another 164a is under the right base beam 156. In addition, a second pair of wheels 164b is preferably positioned at an intermediate position along the length of the support platform 100, 100', 100", such as along a mid-axis MA-MA of base 120. Again, one wheel 164b is preferably located under the left side of the platform, and another wheel 164b is located under the right side of the support platform 100, 100', 100". Finally, a third set of wheels 164c is preferably located toward a front portion 152 of the support platform 100, 100', 100". In at least one embodiment of the invention, the front wheels 164c are set closer to a center longitudinal axis C-C of the platform as compared to the first and second pairs of wheels 164a, 164b at the rear and intermediate positions along the support platform 100, 100', 100". In accordance with at least one embodiment of the invention, the third set of wheels 164c preferably comprise a larger diameter than at least one of the first pair of wheels 164a and the second pair or wheels 164b. In addition, for the wheel configuration shown in FIG. 7, the first wheels 164a on the right and left sides are substantially equidistant from the center longitudinal axis C-C as the second wheels 164b on both the right and left sides of the support platform 100, 100', 100".

Figure 8:
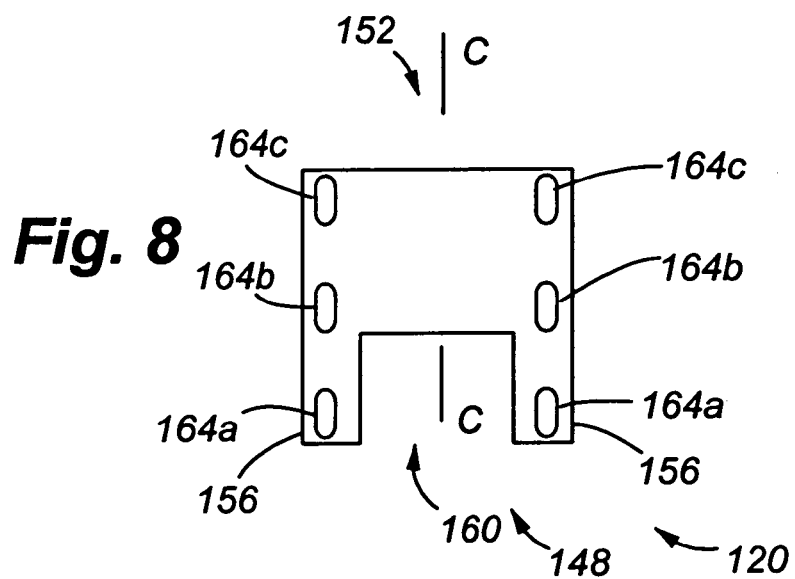
FIGS. 8 and 9 are bottom views of alternate wheel orientations and platform base shapes.
Figure 9:
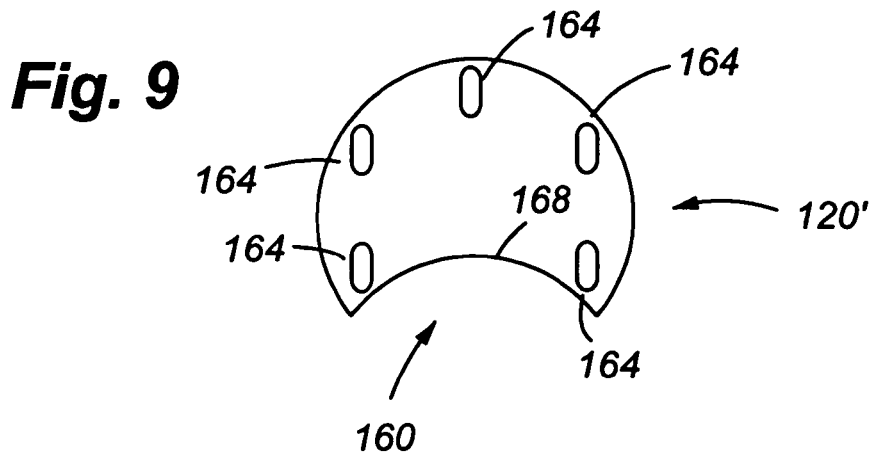

Referring now to FIGS. 8 and 9, and in accordance with embodiments of the present invention, alternative arrangements of the wheels 164 are within the scope of the present invention. FIG. 8 depicts a configuration wherein the wheels 164a, 164b, and 164c are all equidistant from the center longitudinal axis C-C of the support platform 100, 100', 100". With regard to FIG. 9, a modified shape of the base is shown as base 120'. Base 120' is shown with five wheels 164, wherein the base 120' has a substantially circular footprint but with an arcuate shaped opening 160 bounded by an arcuate shaped front base portion 168 for the patient's feet as they walk with the support platform 100, 100', 100". Other configurations of the base are considered within the scope of the present invention.

In accordance with various embodiments of the present invention, the wheel positions includes alternate configurations designed to best address the issues of overcoming a raised obstacle such as a carpet/tile transition or door threshold, spanning a gap such as an elevator threshold, maintaining extreme maneuverability in areas with limited space, and maintaining directional tracking to aid with control as a patient ambulates. Accordingly, the alternative wheel configurations of the present invention provide for advantageous maneuverability and stability, and thus increased safety for the patient using the support platform 100, 100', 100".

The wheels 164 are preferably sized to provide added stability to the support platform 100, 100', 100". Accordingly, wheels 164 are preferably between about 2 to 10 inches in diameter, and more preferably between about 3 to 9 inches in diameter, and more preferably yet, a combination of wheels with the smaller wheels 164a, 164b measuring about 3 to 5 inches in diameter and the larger wheels 164c measuring about 7 to 8 inches in diameter.

Referring again to FIGS. 1-3, the platform handle 108 is an integral part of the support platform 100, 100', 100". In at least one embodiment of the invention, the handle 108 comprises a particular ergonomic design that allows the user to push and use the platform while their hands are kept in a comfortable position. The design also minimizes the ability of the user to tip the platform when applying a force to the platform handle 108.

In accordance with another aspect of the invention, the support platform 100, 100', 100" includes a platform top 112 for holding a number of optional components (also referred as "ancillary devices") as discussed hereafter. The platform top 112 is preferably operatively interconnected to a means for holding an IV bag. The means for holding an IV bag preferably includes at least a section of a pole 176, and/or a hook 180, and/or a rail 132, and/or the skirt 136 with a carabiner clip, and/or other hook attachment located either above or below the platform top 112. Additionally, existing IV, enteral and syringe pumps used by health-care facilities will be accommodated on either a pole 176 or rail system 132 located on top of the platform top 112. The support platform 100, 100', 100" will be able to accommodate from zero to six pumps, and more preferably zero to four pumps. For the embodiments depicted in FIGS. 1-5, various maintenance and treatment devices are hung or otherwise interconnected to the support platform 100, 100', 100", on the rails 132, resting on the top 112, or hanging from the skirt 136.

In accordance with embodiments of the present invention, an attachment device comprising a custom carabiner may be provided and used to releasably attach IV bags or other medical equipment, such as an infusion pump, to the platform's support structure. For example, such attachment devices may be used both on the rail 132 or the skirt 136 the support platform 100, 100', 100". In accordance with at least one embodiment of the present invention, the carabiners provide adequate gate clearance to accommodate both the rail 132 or skirt 136, and provide easy interconnectivity and removability of the previously listed devices or IV bags from the support platform 100, 100', 100". In another aspect of the invention, the carabiners preferably comprise of different colors in order to categorize IV fluids for rapid easy identification by healthcare providers. For example, IV fluids without added medication may hang from blue carabiners, IV fluids with antibiotic additives may hang from green carabiners, and IV fluids containing vasopressor additives my hang from red carabiners.

The platform top 112 or other portions of the frame 104 can include one or more other devices or apparatus, including such items as fluid reservoirs, metering pumps, cup/bottle holders, trays, a sitting stool, monitoring devices, computers, and communication devices, as well as a television, camera, phone or radio. Power receptacles 184 may also be provided either associated with the platform top 112 or frame 104 that will allow for multiple electronic devices to be plugged into either side of the platform. The consumer may or may not decide the number of receptacles. In addition, a retractable power cord 188 may also be provided on the support platform 100, 100', 100".

In a separate aspect of the invention, the support platform 100, 100', 100" preferably includes communication equipment to receive vital sign information from the patient by wired or wireless means. The information may then be transmitted wirelessly to the appropriate medical staff or alarm systems while the patient is using the support platform 100, 100', 100". The support platform 100, 100', 100" preferably is interconnected to a stationary outlet while at the patient's bed, and then when disconnected to allow movement, the on-board communication system preferably provides wireless signals.

The vital sign collection equipment is considered an integral part of the invention as these interact explicitly with the support platform 100, 100', 100". The devices gather information regarding a patient's heart rate, non-invasive blood pressure, arterial blood pressure, central venous pressure, urine output, abdominal compartment pressure, respiratory rate, oxygen saturation and any other information that may be relevant to a patient's care. Other data from devices such as the bed and ventilator to include patient weight, bed alarms and ventilator parameters may be received and transmitted through the support platform as well.

In a separate aspect of the invention, the support platform 100, 100', 100" preferably includes an on-board oxygen supply 192. In use, for those patients needing an oxygen supply, the tubing is preferably directly interconnected to the patient. The oxygen supply may be an existing oxygen bottle system or preferably includes tubing connections to allow the support platform 100, 100', 100" to be interconnected to a stationary oxygen source, such as a wall outlet that carries and delivers oxygen to a patient's hospital room. Accordingly, the support platform 100, 100', 100" can be positioned at the side of the patient's bed, and when the patient leaves his or her bed, the tubing from the support platform 100, 100', 100" is disconnected from the stationary oxygen source, without substantial interruption in the flow of oxygen to the patient. Accordingly, the support platform 100, 100', 100" preferably includes a bypass connection for utilizing a stationary oxygen source when the support platform 100, 100', 100" has tubing interconnected to the stationary oxygen source.

In yet a separate aspect of the invention, the support platforms 100, 100', 100" preferably includes a chargeable battery and/or chargeable uninterruptible power supply, (where a chargeable battery and/or chargeable uninterruptible power supply is herein referred to collectively or singularly simply as "UPS") 200. The UPS 200 is preferably located near the base 120 to provide a relatively low center of gravity for the support platform 100, 100', 100". The UPS 200 allows the support platform 100, 100', 100" to be unplugged from a stationary power source, such as a wall outlet, with the platform's UPS 200 maintaining power to all of the on-board systems, such as the injection pumps, suction pumps, and vital sign monitoring equipment. In addition, the UPS 200 provides a back-up power supply to the electronic devices interconnected to it. Therefore, in the event of a power outage, the UPS 200 provides emergency power to the electrical devices interconnected to the platform's UPS 200. This is particularly advantageous for site locations that do not have an emergency back-up generator connected to the building's power supply. Preferably, the UPS 200 charges when it is plugged into a wall outlet while the devices remain operational.

For platforms utilizing electrical devices, the support platform 100, 100', 100" is preferably pre-wired and includes an electrical system. Therefore, the support platform's built-in modularity and electrical system limits the number of cords to power the modular electrical devices, such as pumps or monitoring devices. Accordingly, in one preferred embodiment, injection pumps, suction pumps, monitoring devices, and/or communication equipment can be quickly snapped into place into the frame 104 of support platform 100, 100', 100", such as in the platform top 112 of the support platform, with the power supply to the subject device provided by the hook-up port 184 or receiving connector on the support platform 100, 100', 100".

In a separate aspect of the invention, the support platform 100, 100', 100" preferably includes an umbilical cord (not shown) having common plug for interconnecting a plurality of systems to a single outlet, such as a wall outlet. The umbilical cord may include a variety of systems, including electrical power, oxygen, suction, and/or a communication connection. When the patient uses the support platform 100, 100', 100" as a walking aid, or when the patient is moved in their bed with the support platform 100, 100', 100" interconnected to the bed or the support platform 100, 100', 100" is otherwise made mobile, the common plug is removed from the wall outlet, thereby not only freeing the support platform from being tethered to the wall, but also engaging the on-board UPS 200 to power any interconnected devices, as well as engaging the on-board oxygen supply and suction pump to the patient, if in use. Therefore, the umbilical cord and associated common plug allows for a quick and easy disengagement from a stationary hook-up. In addition, in order to engage the support platform 100, 100', 100" to the systems available from a stationary source, such as a wall outlet, the common plug attached to the umbilical cord is simply engaged with the wall outlet, thus bypassing and/or recharging the support platform's on-board systems.

In yet a separate aspect of the invention, the support platform 100, 100', 100" preferably includes tube and wiring bundling channels or clips to organize the various tubes or wires that lead from the platform to the patient. The tube and wiring bundles are preferably situated to minimize the potential for the tubes or wires to interfere with objects as the support platform 100, 100', 100" is pushed by the patient or the patient is transferred by other personnel.

In yet a separate aspect of the invention, a hip or other body attachment (not shown) or aid can be provided to assist a patient in moving the support platform when the patient has a physical impediment to grasping the platform handle 108, such as may be the case if the patient has a broken arm, leg, pelvis, shoulder, scapula or ribs. Other physical impairments such as arm and leg amputations can be addressed with other attachments either to the platform or patient. A hip attachment would be one such attachment that would interconnect the support platform 100, 100', 100" to the patient, such as by a cushioned bar positioned at or near the patient's hip.

In a separate aspect of the invention, the support platform may include an interior space and/or compartments for holding reservoirs or bags. For example, as shown in FIGS. 2-5, the support platform 100', 100" may include a cabinet area 204 or other enclosure, the cabinet area 204 preferably including one or more drawers 208, doors 212 and/or access panels 216. Hooks or modular receptacles can be provided within the cabinet space. The interior space or cabinet area 204 can be configured to receive one or more urine or drainage bags. More preferably, in accordance with embodiments of the invention, the collection chambers can accommodate canister assemblies (not shown) designed to provide a mechanism of measuring the volume of the canisters automatically. This system may include a float, conduction or transmission mechanism. This information could then be converted to electronic data that could be transmitted along with other patient vital statistics as described elsewhere in this document.

Referring now to FIGS. 10-14, and in accordance with another aspect of the invention, the support platform 100, 100', 100" comprises a mechanism for being releasably attached to another object, such as a bed, hand rail, vehicle, etc. In accordance with at least one embodiment of the invention, support platform 100, 100', 100" includes at least one bed hook 1000, and more preferably, a plurality of bed hooks 1000. The bed hooks 1000 provide a means for temporarily docking the support platform 100, 100', 100" to a bed when the platform is not being used as walker by a patient. The bed hooks 1000 allow the support platform 100, 100', 100" to remain stationary and attached to the patient's bed if it is inadvertently bumped by a hospital staff member, patient, or visitor. In addition, the bed hooks 1000 can be used to secure the support platform to the patient's bed if the patient is moved while remaining within the bed and the support platform is required to move with the bed. For this type of use, an additional staff member is not needed to roll the support platform 100, 100', 100" adjacent to the moving bed. The bed hooks 1000 allow the support platform 100, 100', 100" to be lifted by another object, such as the patient's bed, such that the wheels 164 the platform are suspended, thereby making transportation easier because only the wheels on the bed need be controlled.

Figure 10:
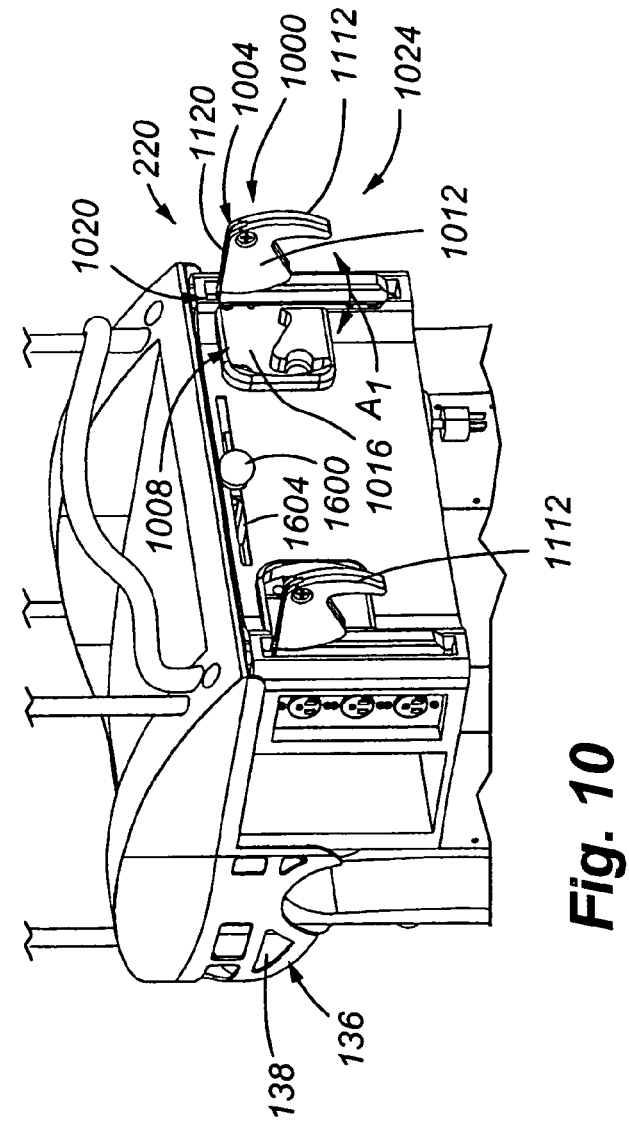
FIG. 10 is a partial enlarged rear perspective view of an upper portion of the platform shown in FIG. 3.

Referring now to FIGS. 5 and 10, an upper portion 220 of a support platform 100, 100', 100" is shown that includes a pair of bed hooks 1000, wherein a first bed hook 1000 is located adjacent to or at a right side of the support platform 100, 100', 100" and a second bed hook 1000 is located adjacent to or at a left side of the support platform 100, 100', 100". For the embodiment of the support platform 100" shown in FIGS. 3-5, the bed hooks 1000 are located at the rear portion 148 of the support platform 100". However, it is to be understood that the bed hooks 1000 may be used on any version of the support platform, including support platform 100, 100', 100", and furthermore, the bed hooks 1000 may be located not only at the rear 148 of the support platform, but also at the front 152 or along a side of the support platform.

Each bed hook 1000 preferably includes an arm member 1004 that is rotatable in at least one direction, or outward from the support platform, such as per arrow $A_1$. In addition, at least a portion of the arm member 1004 is also rotatable in a second direction when engaging a bed or other object to which it is being attached, such as per arrow $A_2$. More particularly, and as described in additional detail below, the arm member 1004 is first rotated to extend away from the platform, as per arrow $A_1$, and then the arm member 1004 may be rotated again as per arrow $A_2$ to engage the bed or other object. As shown in FIG. 10, arm member 1004 is preferably located in a retracted or first position 1008, wherein the arm member 1004 is closed or positioned substantially adjacent the upper portion 220 of the support platform 100, 100', 100". More particularly, when closed, a side surface 1012 of the arm member 1004 is situated adjacent a rear side 1016 of the support platform 100, 100', 100". The arm member 1004 is then rotated on a hinge 1020 to an open or second position 1024 for engagement with an object, such as a bed. Thus, the bed hooks 1000 preferably feature a plurality of positions so that they remain unobtrusive when not in use. In addition, the bed hooks 1000 preferably include a material suitable for gripping, such as a plastic or rubber pad (not shown).

Figure 11A:
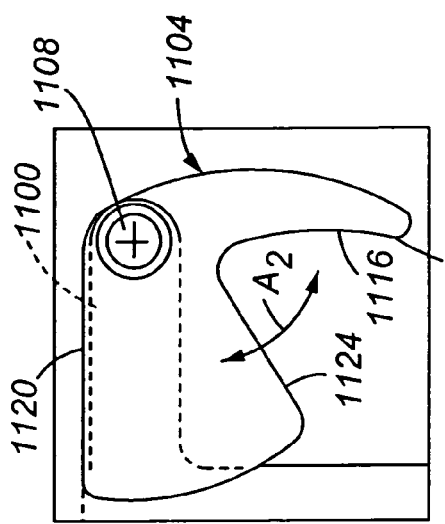
FIGS. 11A and 11B are side elevation views of an embodiment of a bed hook.
Figure 11B:
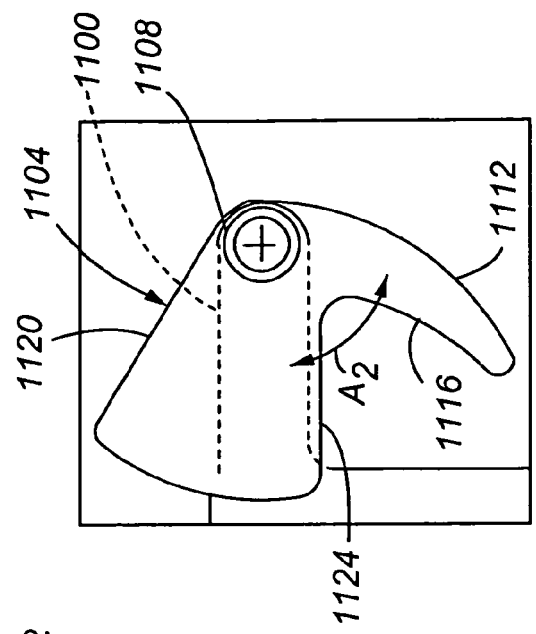

Referring now to FIGS. 11A and 11B, the arm member 1004 is shown in an extended or open position 1024. In accordance with embodiments of the present invention, the arm member 1004 includes a lateral branch 1100 and a rotatable gripper portion 1104. The gripper portion 1104 is rotatably interconnected to the lateral branch 1100 by a pin 1108. In accordance with embodiments of the present invention, the gripper portion 1104 includes a pinching finger 1112 that has an inside surface 1116 for contacting the bed or object to which the support platform 100, 100', 100" is to be attached. In addition, the gripper portion 1104 further includes an upper finger 1120 with an underside 1124 for also contacting the bed or object to which the support platform is to be attached. As shown in FIG. 11A, the gripper portion 1104 is in an unhooked position 1128. Upon rotation of the gripper portion 1104 about pin 1108, the pinching finger 1112 moves toward the support platform to clamp or engage the bed.

Figure 14:
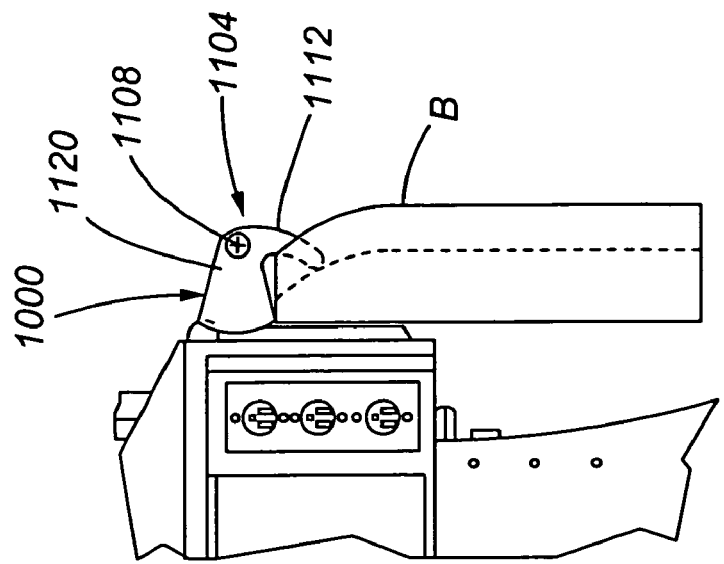
FIGS. 12-14 are side elevation views of the bed hook of FIGS. 11A and 11B in various operable positions with a bed.
Figure 13:
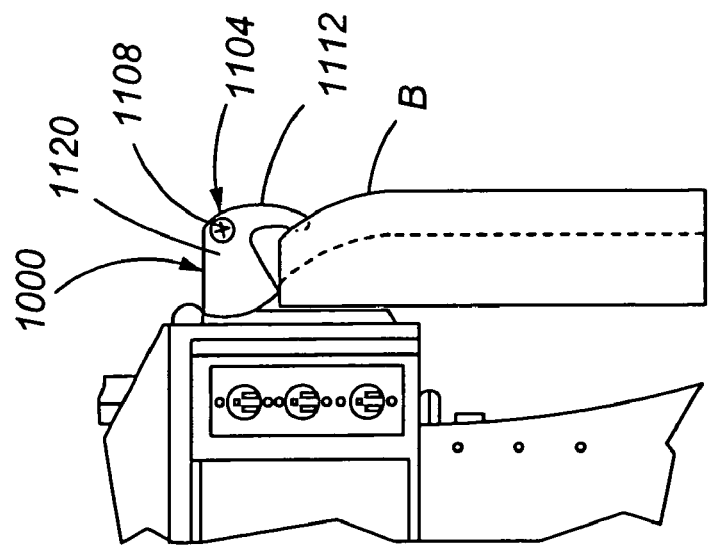
Figure 12:
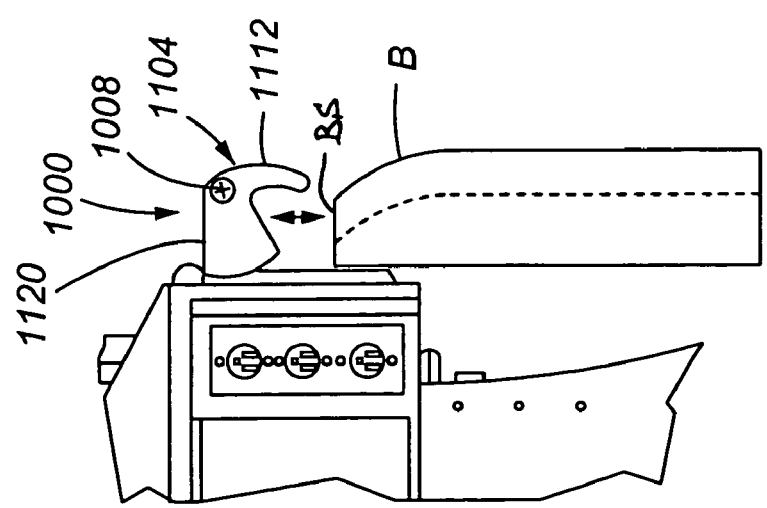

Referring now to FIGS. 12-14, a support platform 100, 100', 100" with bed hooks 1000 is shown in use. As shown in FIG. 12, the bed hooks 1000 are depicted in the open position 1024 prior to engaging a portion of the bed B, such as a head board, foot board or rail. The portion of the bed B to engage the support platform 100, 100', 100" is then raised. As seen in FIG. 13, an upper surface BS of the bed B contacts the underside 1124 of the upper finger 1120 of the gripper portion 1104. Referring now to FIG. 14, as the bed B is raised further, the gripper portion 1104 rotates about pin 1108 relative to the lateral branch 1100. In so doing, the pinching finger 1112 rotates toward the rear side 1016 of the support platform 100, 100', 100", thereby pinching the bed B between the inside surface 1112 of the pinching finger and the rear surface 1016 of the support platform 100, 100', 100". With continued raising the bed B, the bed B will lift the support platform 100, 100', 100" from the floor. The bed B can then be moved with the support platform 100, 100', 100" releasably attached to the bed B. The bed hooks 1000 thus provide a means for moving the platform and the bed as a unit, without the need for a separate attendant or nurse to guide the support platform as another person moves the bed.

In accordance with embodiments of the present invention, an alternative attachment device (not shown) may be used to releasably attach the support platform 100, 100', 100" to a bed or other object. For example, the platform handle 108 may be modified for engaging a portion the bed or another object. Such alternative attachment device may include an adjustable setting that allows the alternative attachment device to be configured for use with a variety of bed frames or wheelchair configurations or other vehicles, such as automobiles or motorized platforms.

Figure 15:
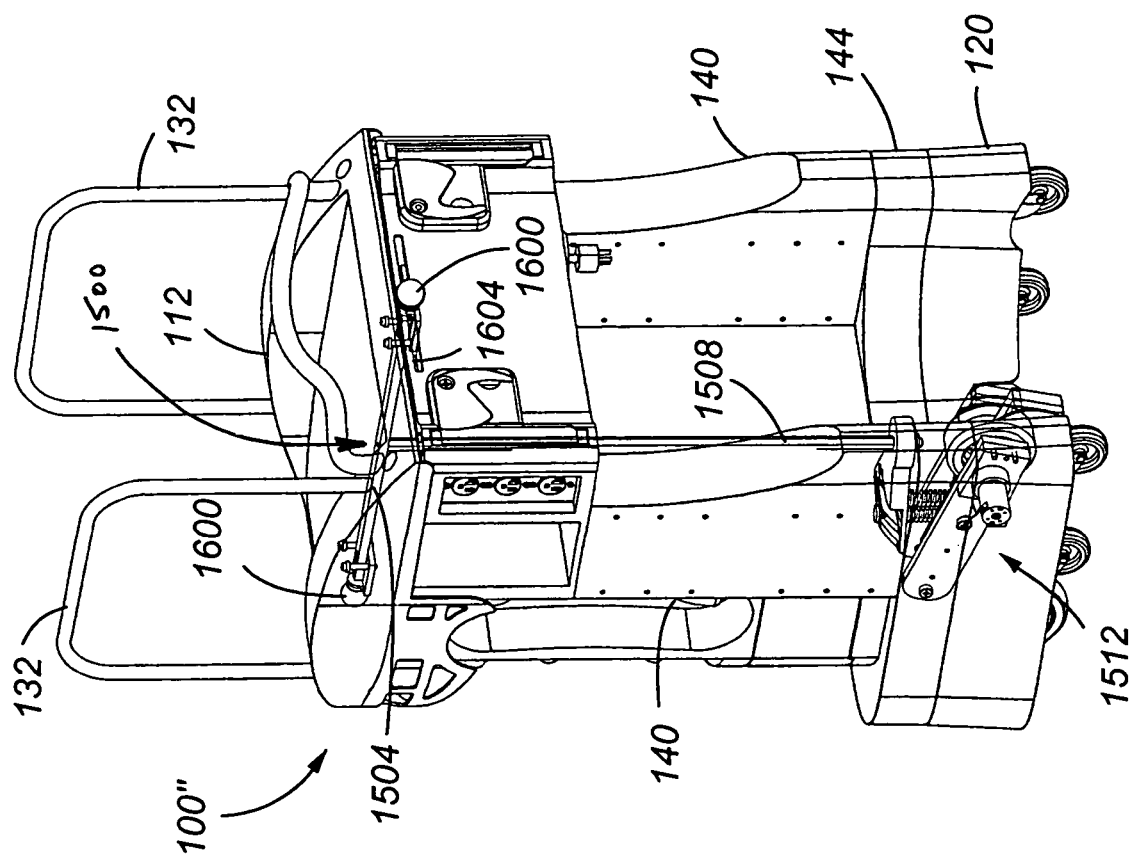
FIG. 15 is a transparent rear perspective view of the platform shown in FIG. 3, wherein the platform structure is superimposed over an embodiment of a transmission system.

Referring now to FIG. 15, and in accordance with at least one embodiment of the invention, the support platform 100, 100', 100" may include a selectable transmission system 1500. FIG. 15 illustrates a number of components of the transmission system 1500 in solid lines, with other aspects of the support platform 100, 100', 100" superimposed over the transmission system. It is to be understood that the transmission system 1500 is also applicable to support platform 100, 100', 100", as well as other platforms that embody the present invention.

In general, the transmission system 1500 comprises a selectable control bar 1504 that is connected to a control shaft 1508 that controls a transmission applicator mechanism 1512. In accordance with embodiments of the present invention, transmission system 1500 preferably has a plurality of settings or modes that can be selected using the control bar 1504. For the embodiments illustrated in FIGS. 15-21, three different settings are provided; however, it is to be understood that a transmission system with an alternate number of settings is possible, such as two settings.

Figure 16:
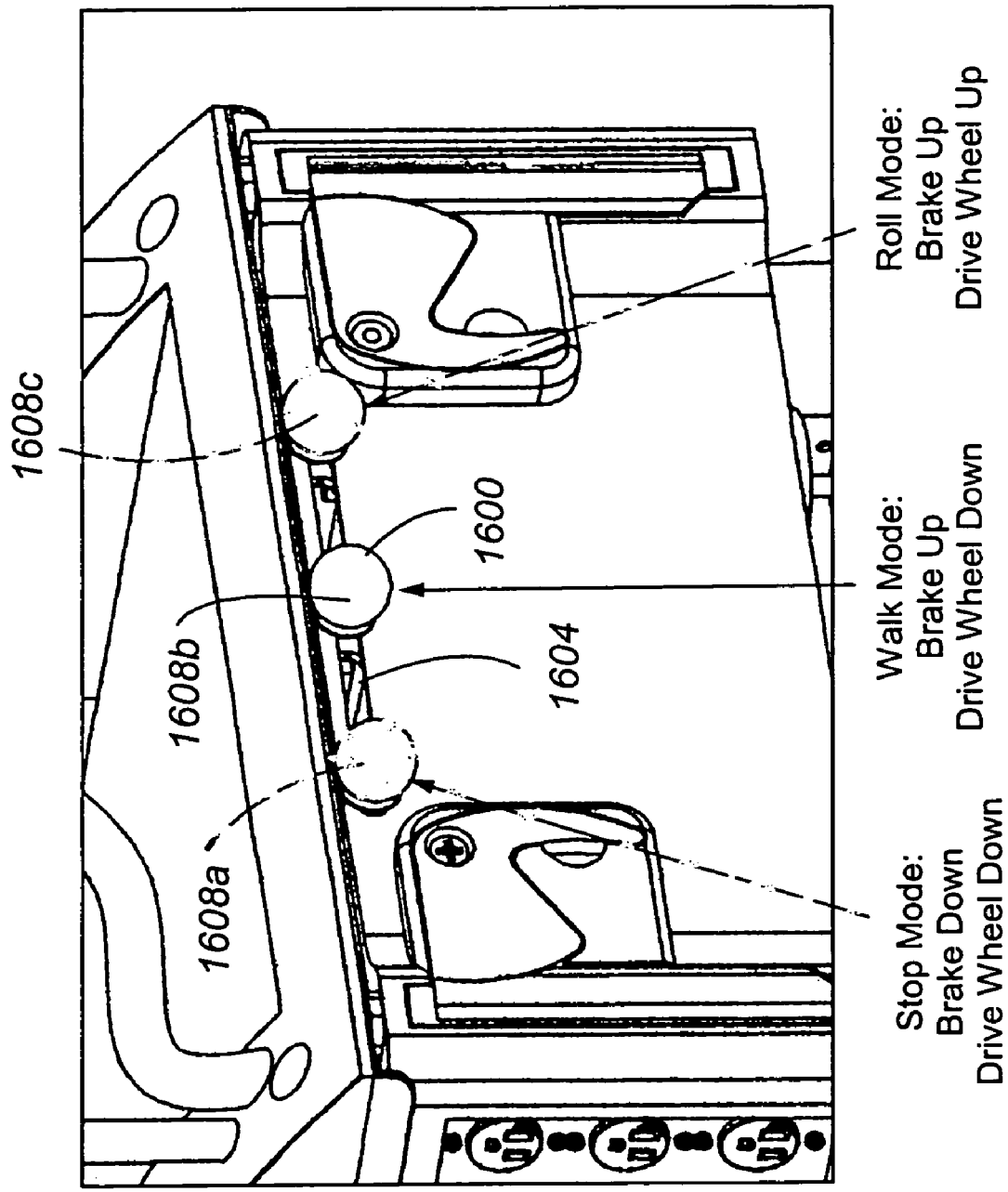
FIG. 16 is a partial enlarged rear perspective view of the platform shown in FIG. 15, wherein the handle of the transmission control mechanism is shown in its alternate positions.
Figure 17:
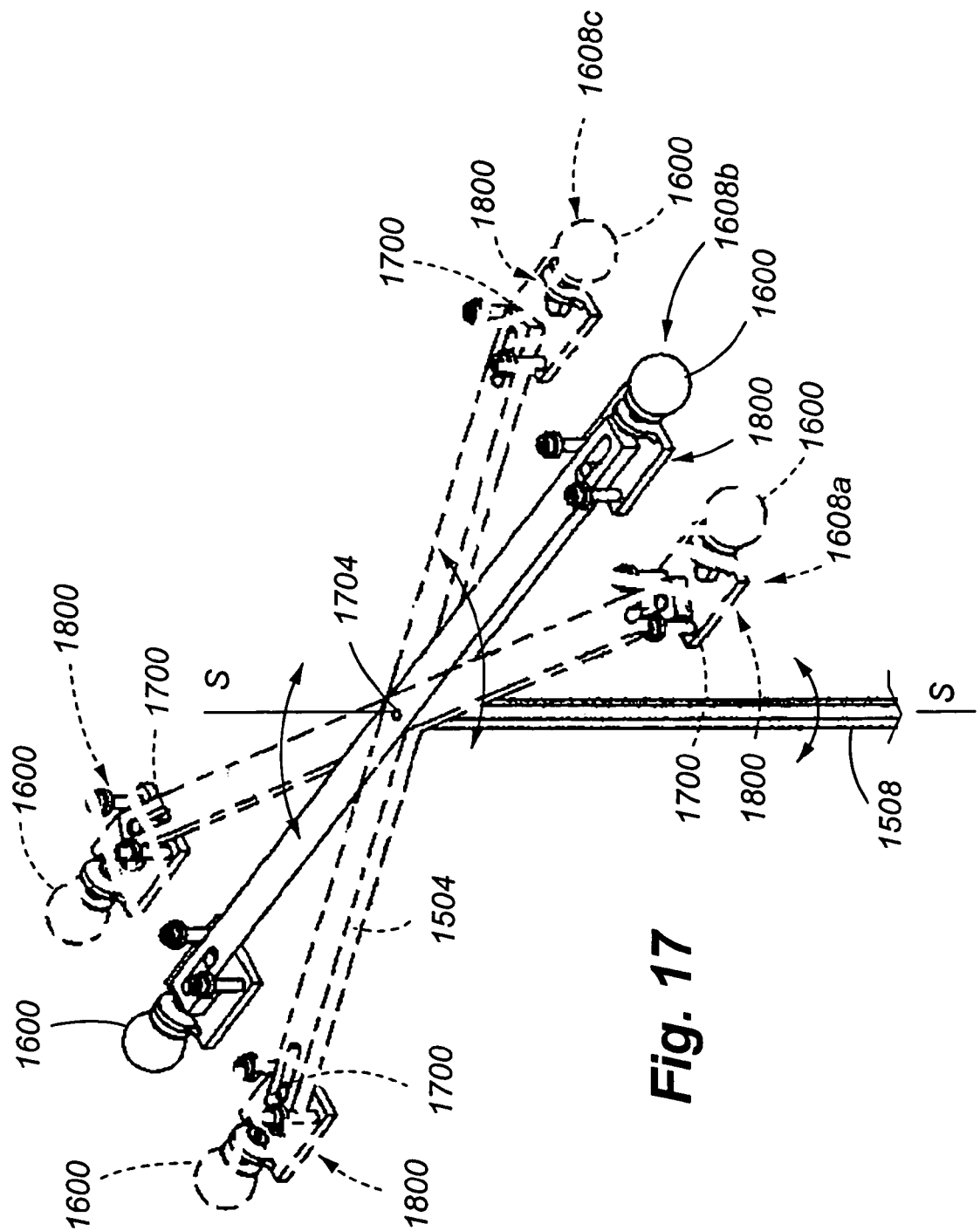
FIG. 17 is a perspective view of alternate positions of the transmission control mechanism shown in FIG. 15.

Referring now to FIGS. 16 and 17 that each show a portion of the transmission system 1500, the control bar 1504 is preferably interconnected to a handle 1600, wherein the handle 1600 is movable along slot 1604, thereby allowing a user or healthcare staff member to select the setting for the transmission system 1500. More particularly, as shown in FIG. 16, a first setting corresponds to a stop mode, a second setting corresponds to a walk mode, and a third setting corresponds to a roll mode. In accordance with the embodiment and view shown in FIG. 16, the stop mode is the left-most position 1608a shown for the handle 1600, the walk mode is an intermediate position 1608b shown for handle 1600, and the roll mode is the right-most position 1608c shown for handle 1600. In general, the stop mode corresponds to having the support platform 100, 100', 100" stationary, the walk mode corresponds to placing the support platform 100, 100', 100" in a controlled state for a patient to ambulate using the support platform 100, 100', 100" as a walking aid, and the roll mode corresponds to a free-rolling state wherein the support platform 100, 100', 100" can be quickly and easily rolled, such as by a healthcare staff member moving the support platform 100, 100', 100" to a patient's room from a storage area.

Figure 18:
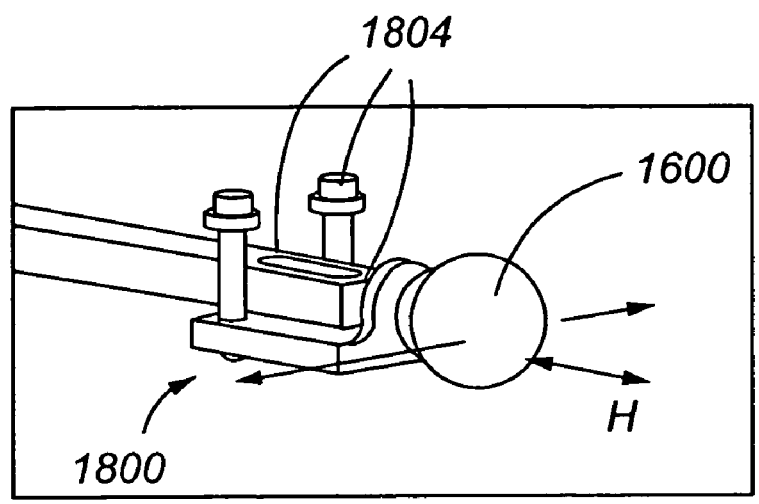
FIG. 18 is an enlarged perspective view of a portion of the device shown in FIG. 17.

In accordance with embodiments of the present invention, and as best seen in FIGS. 17 and 18, although not required, a second handle 1600 may be positioned at the front of the support platform 100, 100', 100" to allow control of the transmission system 1500 from the front of the support platform 100, 100', 100". This configuration offers several advantages, including that a healthcare staff member can set the transmission system 1500 when a patient is at the rear of the support platform 100, 100', 100" and substantially blocking the handle 1600 at the rear of the support platform 100, 100', 100". Whether at the front or back of the support platform 100, 100', 100", the handle 1600 is generally moved transversely to a vertical axis V-V of the support platform 100, 100', 100" within the slot 1604. The handle 1600 is preferably interconnected to the control bar 1504 using an interconnection mechanism 1800 comprising connecting hardware 1804 that allows an end 1700 of the control bar 1504 to rotate relative to the handle 1600, such that a longitudinal axis H-H of the handle 1600 remains substantially parallel to a front to rear axis A-A of the support platform 100, 100', 100" as the handle 1600 is moved along slot 1604. The control bar 1504 rotates at pivot point 1704 about a rotational axis that corresponds to the longitudinal axis S-S of the control shaft 1508. Although only one control shaft 1508 is shown, the control bar 1504 may be interconnected to a plurality of shafts that lead to one or more transmission applicator mechanisms.

Figure 19:
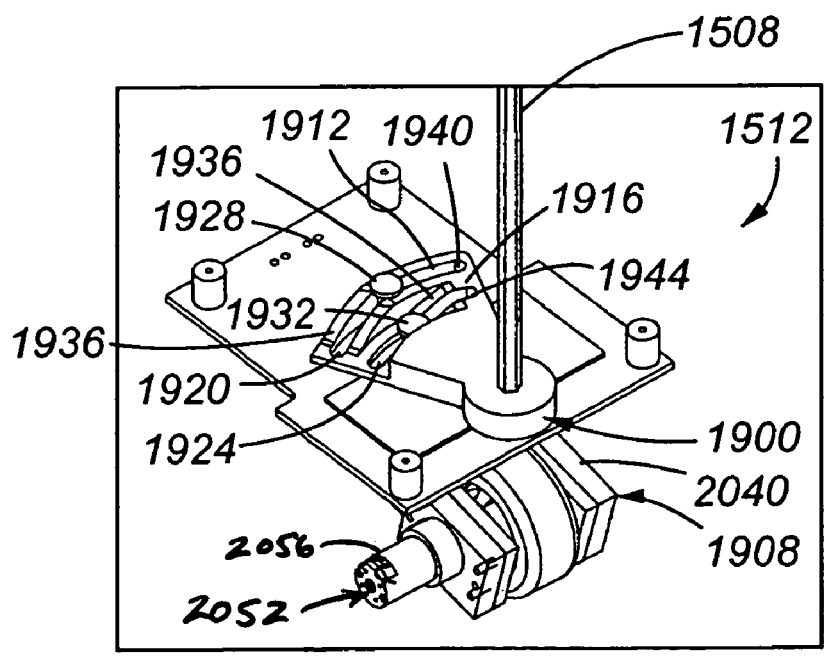
FIG. 19 is a perspective view of a portion of the transmission system shown in FIG. 15.
Figure 20:
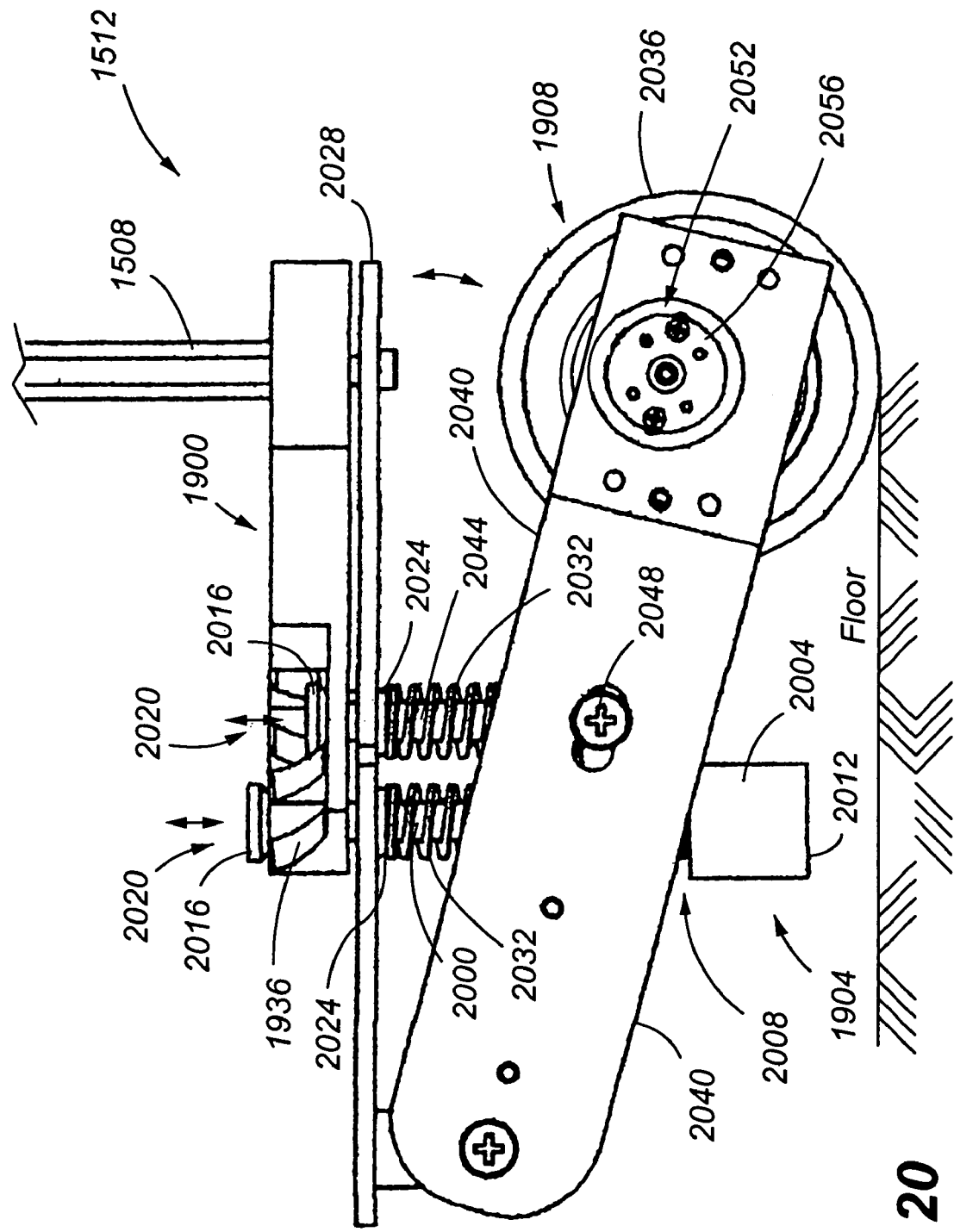
FIG. 20 is an enlarged side elevation view of the device shown in FIG. 19.

Referring now to FIGS. 19 and 20, and in accordance with at least one embodiment of the present invention, a transmission applicator mechanism 1512 is shown that includes functionality corresponding to the three transmission settings of stop mode 1608a, walk mode 1608b and roll mode 1608c. The transmission applicator mechanism 1512 generally includes a cam 1900 that is connected to the control shaft 1508. In at least one embodiment, the cam 1900 provides at least a means for adjusting the position of the drag wheel. When the handle 1600 is moved along slot 1604, the control bar 1504 rotates the control shaft 1508, and the cam 1900 also rotates. As the cam 1900 rotates, the transmission applicator mechanism 1512 either (1) applies both a brake assembly 1904 and a drag wheel assembly 1908 to the floor (or other surface under the platform) when the transmission system 1500 is set to the stop mode 1608a, (2) maintains the brake assembly 1904 in a raised position while the drag wheel assembly 1908 contacts the floor when the transmission system 1500 is in the walk mode 1608b, or (3) maintains both the brake assembly 1904 and the drag wheel assembly 1908 in raised positions while the transmission system 1500 is in the roll mode 1608c.

The brake assembly 1904 may comprise a variety of configurations, and in one embodiment comprises a post 2000 that is connected to a stopper 2004 at the distal end 2008 of the post 2000. The stopper 2004 may comprise a variety of materials and configurations, but generally includes characteristics that will generate a relatively large frictional force with the underlying floor. For example, the stopper 2004 may comprise a rubber or plastic structure that tends to generate a large amount friction with the floor. Although the example stopper 2004 shown in FIG. 20 is cylindrical in shape with a circular distal end 2012 for contacting the floor, the stopper 2004 may be elongated in a direction transverse to the post 2000 such that a relatively wide contact area is formed with the floor. The post 2000 extends from the stopper 2004 to the cam 1900, and includes an upper flange 2016 at its proximal end 2020 at the cam 1900, and a lower flange 2024 that resides adjacent and below a base panel 2028. As will be discussed in more detail below, the brake assembly 1904 also preferably includes a biasing member 2032 that resides between the lower flange 2024 and the stopper 2004. As shown in FIG. 20, and in accordance with at least one embodiment, the biasing member 2032 comprises a compression spring, but may also comprise other structure, such as an air cylinder.

The drag wheel assembly 1908 provides a means for frictionally engaging the underlying surface, and in at least one embodiment comprises a wheel 2036 interconnected to the base panel 2028 by a movable linkage arm 2040, wherein the linkage arm 2040 can be lowered and raised to either apply the wheel 2036 to the floor, or to raise the wheel 2036 from contacting the floor. As discussed in more detail below, the drag wheel assembly 1908 preferably incorporates a rotation resistance mechanism that is interconnected to the wheel 2036 such that the wheel 2036 acts as a governor to control the speed of the support platform 100, 100', 100". The linkage arm 2040 is preferably interconnected to the cam 1900 by a post 2044 that extends from a pivot point 2048 at the linkage arm 2040 to the cam 1900. The post 2044 includes an upper flange 2016 at its proximal end 2020 at the cam 1900, and a lower flange 2024 that resides adjacent and below the base panel 2028. The assembly for the drag wheel assembly 1908 also preferably includes a biasing member 2032 that resides between the lower flange 2024 and the pivot point 2048 at the linkage arm 2040.

Referring still to FIGS. 19 and 20, and in accordance with at least one embodiment of the present invention, the cam 1900 includes a first curved or arc-shaped channel 1912 to control the brake assembly 1904, and a second curved or arc-shaped channel 1916 to control the drag wheel assembly 1908. When handle 1600 is moved to the stop mode 1608a, the control bar 1504 rotates the control shaft 1508 such that the post 2000 of the brake assembly 1904 and the post 2044 of the drag wheel assembly 1908 are located at first positions 1920 and 1924 of the channels 1912 and 1916, respectively. At these first positions 1920 and 1924, both the brake assembly 1904 and the drag wheel assembly 1908 are engaged such that the stopper 2004 and wheel 2036 are in contact with the floor. When at the first position 1920, the post 2000 is in a lowered position because the cam thickness at the first position 1920 is such that the upper flange 2016 of post 2000 is lower relative to the base panel 2028. When in the first position 1920, the biasing member 2032 of post 2000 forces the stopper 2004 downward and in contact with the floor. Similarly, when post 2044 is in the first position 1924, the upper flange 2016 of post 2044 is also lower relative to the base panel 2028 and the biasing member 2032 of post 2044 forces the linkage arm 2040 downward and places the wheel 2036 in contact with the floor.

Upon sliding handle 1600 to the walk mode 1608b position, the control bar 1504 rotates and turns the control shaft 1508, thereby turning the cam 1900. As the cam 1900 is turned, posts 2000 and 2044 remain laterally stationary and traverse the cam 1900 along channels 1912 and 1916, respectively. The posts 2000 and 2044 are then located at the second positions 1928 and 1932 along the first and second channels 1912 and 1916, respectively. In addition, as the proximal end 2020 of post 2000 for the brake assembly 1904 moves along first curved channel 1912 from the first position 1920 toward the second position 1928, the post 2000 rises because the upper flange 2016 of post 2000 encounters cam transition ramp 1936. The rise in cam transition ramp 1936 pulls the stopper 2004 off the floor and compresses the biasing member 2032 between the stopper 2004 and the lower flange 2024. In addition, as the cam 1900 is turned, the post 2044 remains in its lowered position because the elevation of the upper flange 2016 of the post 2044 at the second position 1932 is substantially equal in elevation to the elevation of the upper flange 2016 when the post 2044 is in the first position 1924.

Upon sliding handle 1600 from the walk mode 1608b position to the roll mode 1608c position, the control bar 1504 again rotates and turns the control shaft 1508, thereby once again turning the cam 1900. Once again, the posts 2000 and 2044 remain laterally stationary and traverse the cam 1900 further along channels 1912 and 1916, respectively. The posts 2000 and 2044 are then located at the third positions 1940 and 1944 along the first and second channels 1912 and 1916, respectively. In addition, as the proximal end 2020 of post 2044 for the drag wheel assembly 1908 moves along second curved channel 1916 from the second position 1932 toward the third position 1944, the post 2044 rises because the upper flange 2016 of post 2044 encounters a second cam transition ramp 1936. The rise in cam transition ramp 1936 pulls the linkage arm 2040 upward and the wheel 2036 off the floor and also compresses the biasing member 2032 between the pivot point 2048 of the linkage arm 2040 and the lower flange 2024 of post 2044. In addition, as the cam 1900 is turned from the walk mode 1608b to the roll mode 1608c, the post 2000 remains in its upper position because the elevation of the upper flange 2016 of the post 2000 between the second position 1928 and third position 1940 is substantially equal in elevation.

The biasing members 2032 for both posts 2000 and 2044 place the brake assembly 1904 and the friction wheel assembly 1908 in a preferred state of engagement because the biasing members 2032 tend to force the down the stopper 2004 and the wheel 2036. That is, work has to be done against the biasing member 2032 for post 2000 to move the handle 1600 from the stop mode 1608a to the walk mode 1608b, and work also has to be done against the biasing member 2032 for post 2044 to move the handle 1600 from the walk mode 1608b to the roll mode 1608c. Thus, if a person is operating the support platform 100, 100', 100" in walk mode 1608b, it is relatively easy to place the handle 1600 in stop mode 1608a and apply the stopper 2004 to the floor because the biasing member 2032 of post 2000 tends to want to force the post 2000 and stopper 2004 downward. This is a safety feature of the transmission system 1500.

Figure 21:
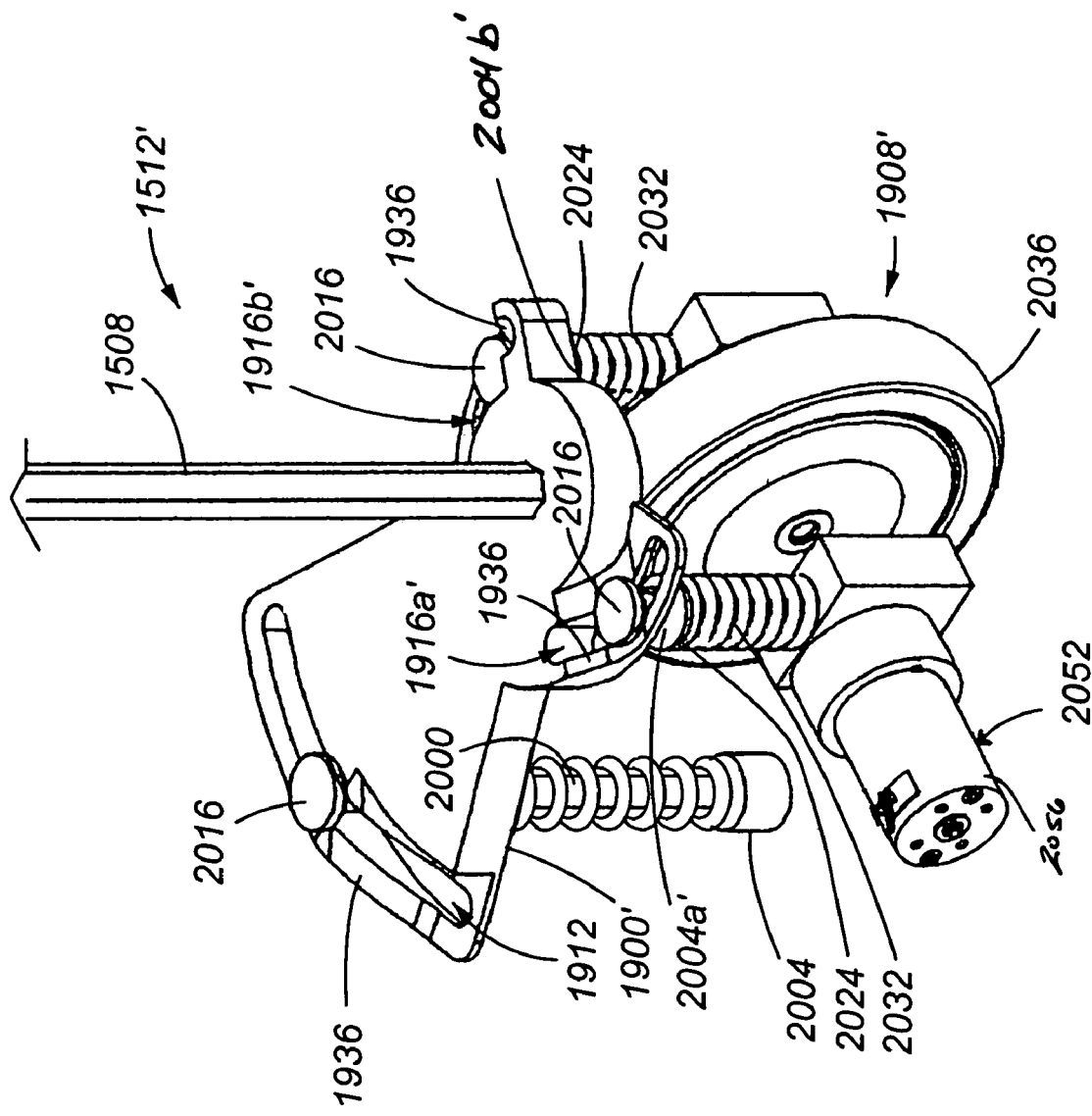
FIG. 21 is perspective view of an alternate embodiment of the device shown in FIG. 19.

Referring now to FIG. 21, an alternate embodiment of a transmission applicator mechanism 1512' is shown. For clarity, the base panel 2028 has been omitted from FIG. 21. Similar to that described above for the assembly 1512 shown in FIGS. 19 and 20, the cam 1900' shown in FIG. 21 includes a first channel 1912 for controlling post 2000 of the brake assembly 1904. The transmission applicator mechanism 1512' further includes a drag wheel assembly 1908' that utilizes two posts 2004a' and 2004b' to control the vertical position of the wheel 2036 through two channels 1916a' and 1916b' in cam 1900'. Although a linkage arm 2040 is not used with transmission applicator mechanism 1512', the operation of the transmission applicator mechanism 1512' is similar to that described above for transmission applicator mechanism 1512. Thus, upon rotation of the cam 1900' in stop mode, the stopper 2004 and wheel 2036 are lowered to contact the floor, and in walk mode the stopper 2004 is raised, while in roll mode both the stopper 2004 and the wheel 2036 are raised from contacting the floor. Thus, the transmission system 1500 may take on a variety of configurations, including alternate transmission applicator mechanisms, and such alternate embodiments and modifications are encompassed by the present invention.

Referring now to FIGS. 20 and 21, and as mentioned above, the drag wheel assembly 1908 preferably includes a rotation resistance mechanism 2052 that is interconnected to the drive wheel 2036, thereby enabling the wheel 2036 to restrict the speed of the support platform 100, 100', 100". In accordance with embodiments of the present invention, the rotation resistance mechanism 2052 may take the form of a friction pad (not shown) that engages at least a portion of the wheel 2036 and/or structure operably interconnected to the wheel 2036. More preferably, however, the rotation resistance mechanism 2052 comprises a braking motor 2056 interconnected to the wheel 2036, such as by way of the wheel's axle. In accordance with embodiments of the present invention, the braking motor 2056 is interconnected to the wheel 2036 through a gearbox. The braking motor 2056 applies a force to the wheel 2036 to slow the wheel 2036 under the principle that little or no wheel speed requires the application of no braking, but high wheel speed requires the application of braking work on the wheel 2036 by the braking motor 2056. More particularly, as wheel speed increases, the output of the braking motor 2056 increases. The increased output results in an increased load on the braking motor 2056, increasing the braking force applied to the wheel 2036. The braking motor 2056 may comprise a permanent magnet DC motor. Furthermore, as can be appreciated by one of skill in the art after consideration of the present invention, the braking motor 2056 is not connected to a source of electrical power, but is instead driven as a generator (i.e., a source of electrical power) by the wheel 2036.

Figure 22:
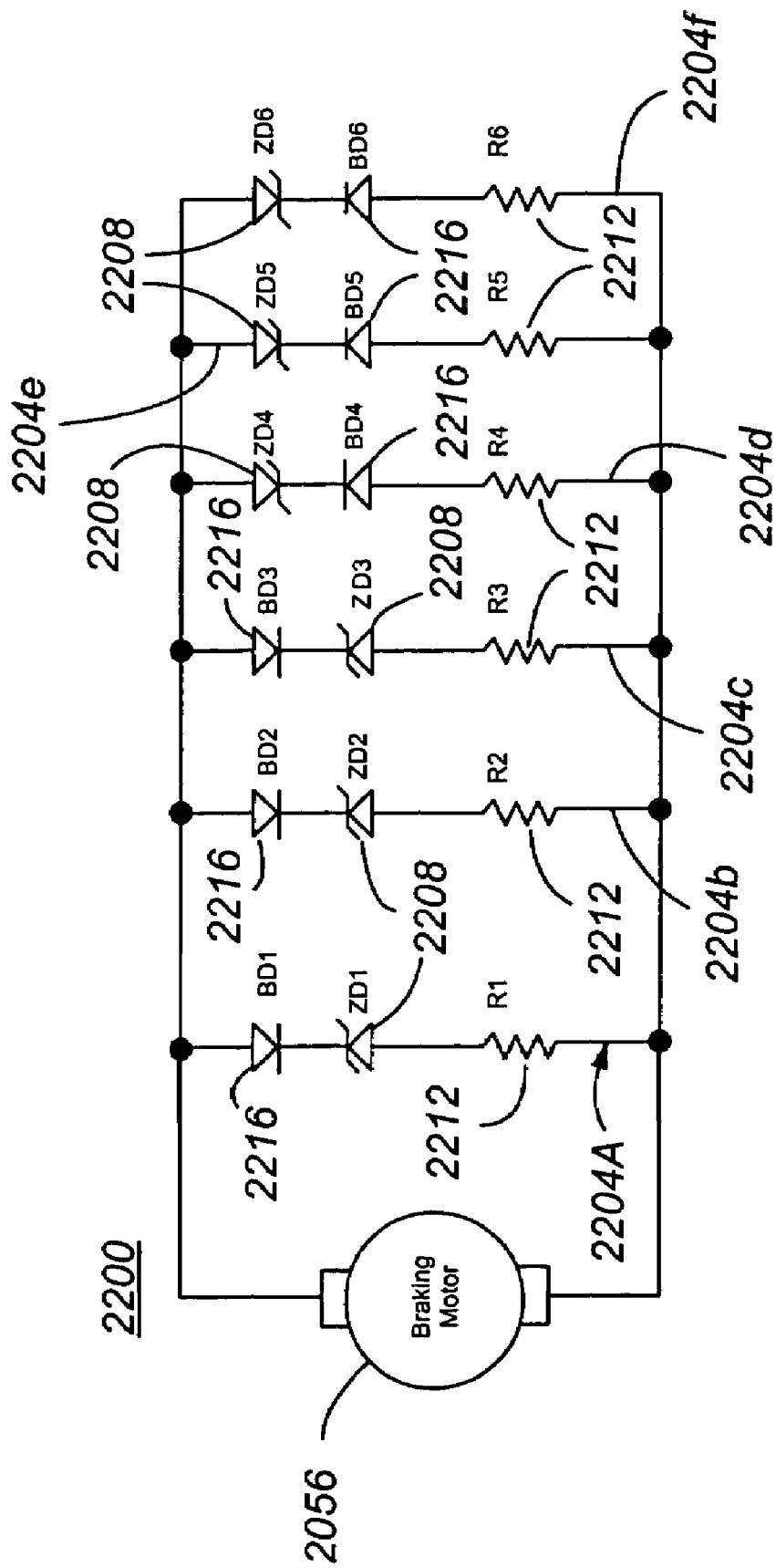
FIGS. 22-25 are various embodiments of motor braking circuits associated with the automatic braking system feature.

Referring now to FIG. 22, a schematic of a motor braking circuit 2200 for applying a braking force to the wheel 2036 in response to a voltage generated by the braking motor 2056 in accordance embodiments of the present invention is illustrated. The circuit shown in FIG. 22 is a multi-stage Zener diode auto-transmission system or braking circuit 2200 for automatically applying a braking force to the wheel 2036. In general, use of a number of different Zener diodes allows different stages of resistance to be applied progressively, as the voltage produced by the motor increases. As can be appreciated by one of skill in the art, the voltage produced by the braking motor 2056 will tend to increase as the rotational velocity of the wheel 2036 driving the braking motor 2056 increases. Furthermore, by switching in additional resistive loads as the voltage produced by the braking motor 2056 increases, and therefore drawing more current, the braking effect of the braking motor 2056 can be increased in steps.

In accordance with embodiments of the present invention, each stage 2204 of the circuit 2200 comprises at least one zener diode 2208 and at least one load resistor 2212. The zener diode ZD1 2208 of the first stage 2204*a* is selected to have a turn on or a breakdown voltage (i.e. a zener voltage) that is relatively low. When the zener voltage is exceeded, the zener diode ZD1 2208 conducts, allowing current to pass through the load resistor R1 2212. Accordingly, the zener diode ZD1 2208 acts as a switching mechanism. The current draw from the introduction of this load will load the braking motor 2056 such that the resistance to rotation of the wheel 2036 (not shown in FIG. 22) will increase essentially linearly with increased speed. The second stage 2204*b* is in parallel with the first stage 2204*a* and has a zener diode ZD2 2208 that is selected to have a zener voltage that is higher than the first zener diode ZD1 2208. If the voltage produced by the braking motor 2056 meets or exceeds the zener voltage of the second zener diode ZD2 2208, the second zener diode ZD2 2208 conducts, allowing current to pass through the load resistor R2 2212 associated with the second stage 2204*b* of the circuit 2200. Accordingly, this zener diode ZD2 2258 also acts as a switching mechanism. Since the first zener voltage is lower than the second zener voltage, the first zener diode ZD1 2208 will continue to conduct while the second zener diode ZD2 2208 is conducting. Accordingly, two current paths through two of the stages 2204 will be active, increasing the rate at which the load increases with increased braking motor 2056 speed as compared to when only the first zener diode ZD1 2208 is conducting. As shown in FIG. 22, additional parallel circuit branches or stages 2204 comprising additional zener diode 2208 and load resistor 2212 pairs can be included, to provide any number of steps in the resistance produced at the wheel 2036 as the rotational speed of the wheel 2036 increases. For example, in FIG. 22 three stages 2204 (stages 2204*a*, 2204*b* and 2204*c*) are included. However, fewer or additional stages 2204 may be included depending on the desired number of steps in the rate of resistance provided by the circuit 2200.

As can be appreciated by one of skill in the art, the zener voltage is generally higher than the voltage at which a zener diode will conduct a forward current. Therefore, if the braking motor 2056 is operated in the opposite direction, such that if a negative voltage is produced at the first terminal of the braking motor 2056, a circuit with branches or stages configured like the first three branches 2204*a-c* of FIG. 22 will allow the load introduced by the associated resistors to be applied at a much lower voltage than when the motor is operated in the other direction. This may be desirable, for example where it is desirable to have the platform move only in a forward direction while in the walk mode. In order to allow for resistance to be applied in a similar fashion in either a forward or reverse direction, blocking diodes 2216 can be introduced in the circuit branches. By introducing blocking diodes 2216, current is only conducted by a stage 2204 when a voltage is applied to that stage's 2204 zener diode 2208 as a reverse voltage, because the blocking diode 2216 will prevent a forward voltage from being applied to this zener diode 2208. Additional circuit branches 2204 can then be provided for progressively introducing a load when the braking motor 2056 is operated in the reverse direction. These additional circuit branches 2204 (see branches 2204*d*, 2204*e* and 2204*f* in FIG. 22) are oriented such that the associated zener diode 2208 and blocking diode 2216 are opposite the orientation of those included in the circuit branches for providing progressively increasing braking force in the forward (opposite) direction (branches 2204*a*, 2204*b* and 2204*c* in FIG. 22). Although only three stages or branches 2204 for applying a braking force in a reverse direction are shown, it should be appreciated that fewer or additional of such stages may be provided.

Figure 23:
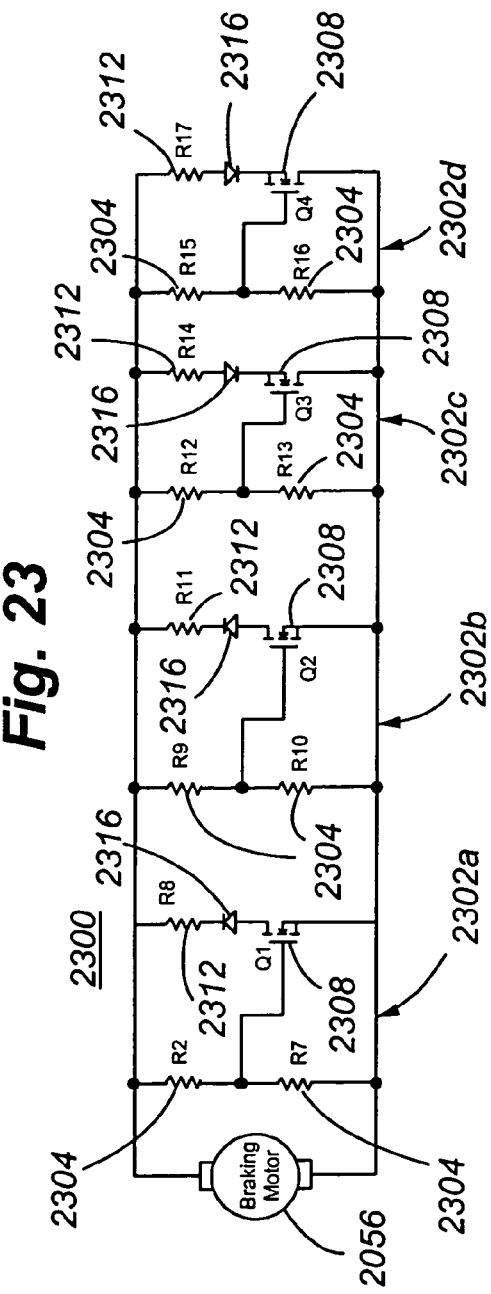

Referring now to FIG. 23, an alternate embodiment for motor braking circuitry is shown. The motor braking circuit 2300 shown in FIG. 23 is a multi-stage metal-oxide semiconductor field-effect transistor (MOSFET) auto-transmission system for automatically applying a braking force to the drive wheel 2036. In general, in the first stage 2302*a*, when the voltage divided down by resistors R2 2304 and R7 2304 is greater than Vth of transistor Q1 2308, transistor Q1 2308 will turn on and apply the load resistor R8 2312 to the braking motor 2056. Accordingly, the voltage dividing resistors 2304 and the transistor 2308 comprise a switching mechanism. Subsequent stages in parallel with the first stage set to different points will add more load in a similar fashion once the set voltage for such stages is met or exceeded. For example, a second stage 2302*b* is illustrated in FIG. 23, which may be configured to turn on at a higher voltage than the first stage 2303*a*. The transistors Q3 and Q4 2308 in the third 2302*c* and fourth 2302*d* stages are set in the opposite direction and will work in the reverse direction. Accordingly, the third and fourth stages 2303 and may be included in order to apply stages of resistance when the braking motor 2056 is turned in a direction opposite the direction the braking motor 2056 is turned to activate the first and second stages 2302*a-b*. Also, the body diodes of the transistors 2308 may be blocked or protected by a blocking diode 2316. Although four stages 2302 are shown in FIG. 23 (two for activation in a forward direction and two for activation in a reverse direction), it should be appreciated that any number of stages 2302 can be provided.

Figure 24:
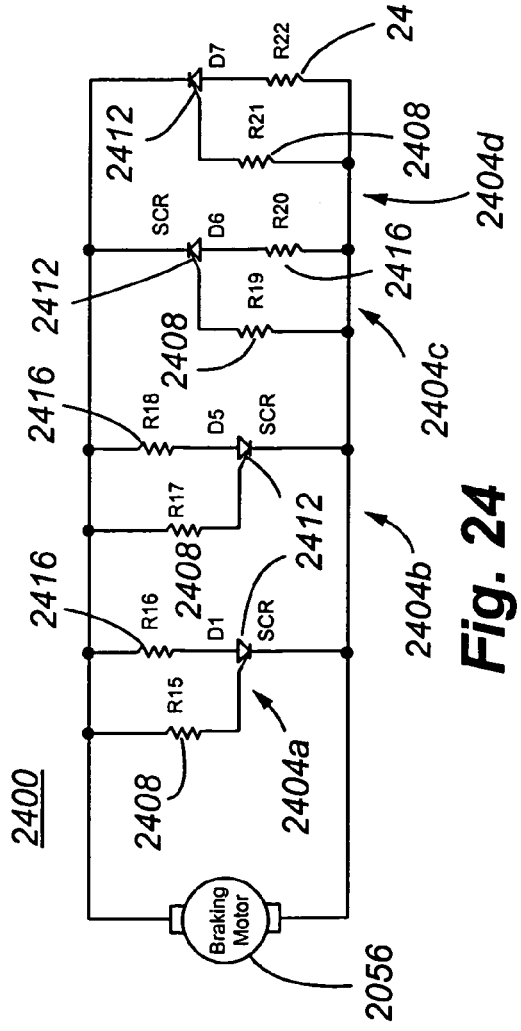

Referring now to FIG. 24, an additional alternate embodiment for motor braking circuitry is shown. The motor braking circuit 2400 shown in FIG. 24 is a multi-stage Silicon Controlled Rectifier (SCR) braking system for automatically applying a braking force to the wheel 2036 (not shown in FIG. 24). In general, in the first stage 2404*a*, when the voltage across resistor R15 2408 gets high enough to send a trigger current through SCR D1 2412 allowing current to pass through load resistor R16 2416, SCR D1 2412 latches on and applies the load resistor R16 2415 to the motor 2056 until the motor voltage drops to the point where there is almost no more current through R16. The SCR 2412 and the resistor 2408 therefore comprise a switching mechanism. The second stage 2404*b*, in parallel with the first stage 2404*a*, has a resistor R17 2408 selected such that a trigger current is not sent through the associated SCR D5 2412 until after the first stage 2404*a* has turned on. Accordingly, the resistance to movement of the braking motor 2056 can be stepped up once the output of the braking motor 2056 exceeds a predetermined amount. Third 2404*c* and fourth 2404*d* stages, each having an SCR 2412 having an orientation that is opposite the orientation of the SCRs 2412 of the first 2404*a* and second 2404*b* stages can be provided to apply stages of braking force in a reverse direction. The third 2404*c* and fourth 2404*d* stages also include trigger resistors R19 and R20 that are connected to an opposite node of the braking motor 2056 as compared to the trigger resistors R15 2408 and R17 2408 of the first 2404*a* and second 2404*b* stages. Although only two stages are shown for providing braking resistance in each direction, it can be appreciated that any number of stages may be provided. Unlike embodiments described in connection with FIGS. 22 and 23, the embodiment illustrated by FIG. 24 does not switch out the load resistor of a stage at the trigger voltage for that stage, but instead retains the current path through the load resistor until a much lower voltage is reached (e.g. almost zero).

Figure 25:
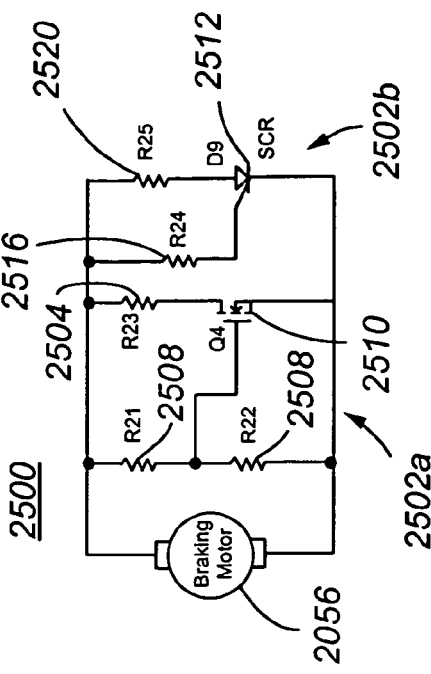

Referring now to FIG. 25, an alternate embodiment for motor braking circuitry is shown. The motor braking circuit 2500 shown in FIG. 25 is a hybrid circuit for automatically applying a braking force to the drive wheel 2036. In general, both an auto-transmission and an auto-braking feature are applied when different set resistances are achieved as a result of the voltage generated by the braking motor 2056. More particularly, the first stage 2502*a* is a stage incorporating a first switching mechanism for introducing a load resistor at a first voltage, while the second stage 2502*b*, which is in parallel with the first stage 2502*a*, incorporates a second switching mechanism for introducing a second load resistor at a second voltage. In the particular example of FIG. 25, the first stage 2502*a* uses a field effect transistor 2510 that allows current to pass through a first load resistor R23 2504 when the voltage divided down by set resistors R21 and R22 2508 is at a selected value. The second stage 2502*b* incorporates a silicon controlled rectifier 2512 that is switched on by a trigger current through resistor R24 2516 when the voltage across that resistor reaches a predetermined value, allowing current to pass through the load resistor R25 2520. The particular arrangement illustrated in FIG. 25 may be useful in selected applications, for example where it is desirable to have a mobile platform brought back to a standstill (or near standstill) after it has reached a velocity that exceeds a pre-determined bound. Specifically, the first stage load resistor R23 2504 can be switched in at a relatively low voltage, while the second load resistor R25 2520 can be switched in at a higher voltage, and the second load resistor will remain switched in until the voltage is almost zero. As can be appreciated by one of skill in the art, additional stages, hybrid or otherwise, can be combined with the illustrated stages 2502*a-b*, for applying a load resistance in the same or in opposite direction from the illustrated stages 2502.

Figure 26:
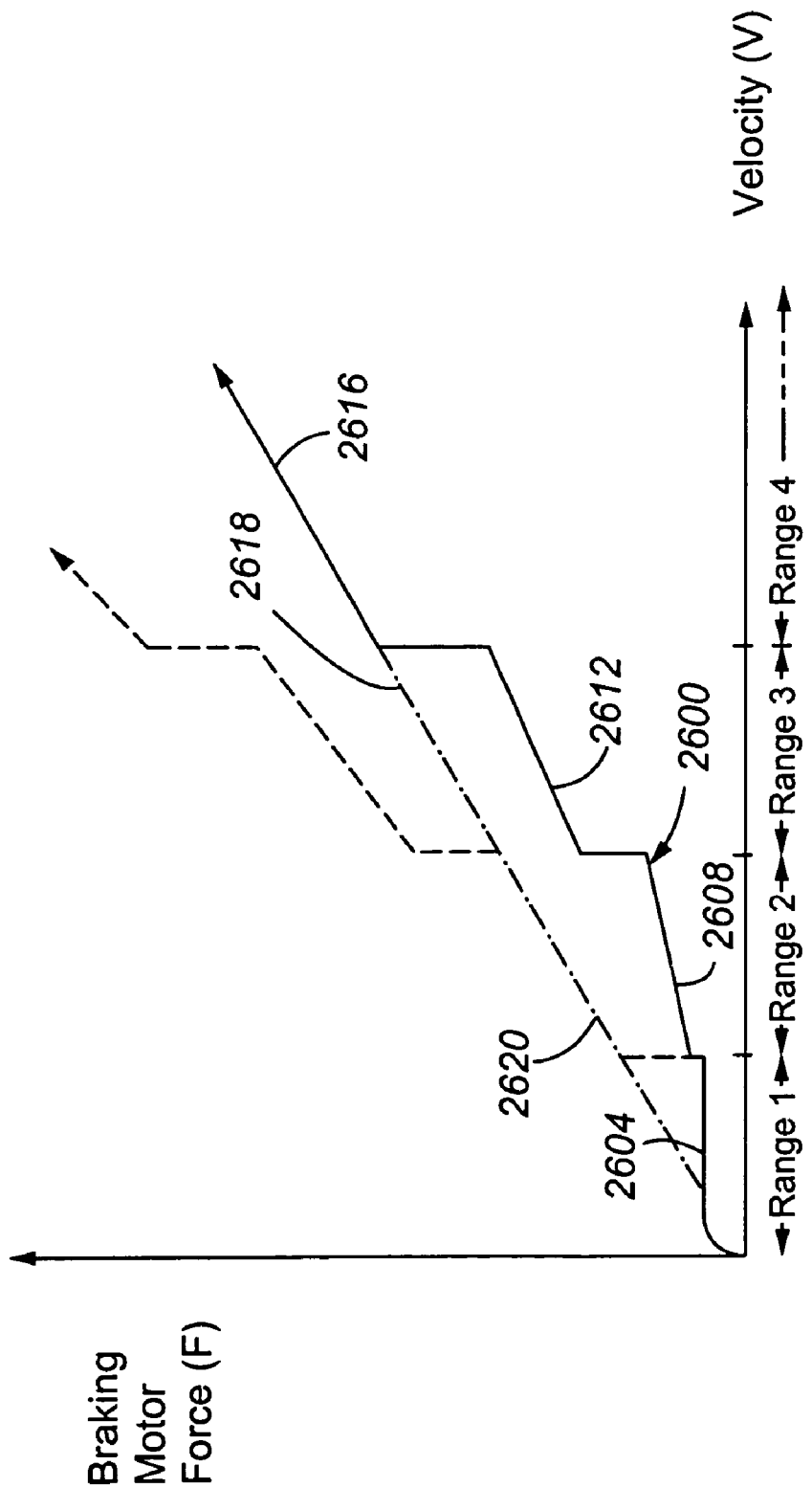
FIG. 26 is a braking force to velocity diagram associated with the automatic braking system feature.

FIG. 26 is a graph depicting how the braking force produced by a braking motor 2056 can be progressively increased with increased braking motor 2055 velocity by using an auto transmission or braking system circuit in accordance with embodiments of the present invention. With specific reference to plot 2600, in a first speed range 2604, the force may remain essentially constant, for example due to the friction of the various platform wheels and of the unloaded braking motor 2056. The first speed range 2604 corresponds to a platform velocity (and therefore a drive wheel 2036 and braking motor 2056 velocity) at which the output produced by the rotation of the braking motor 2056 produces a voltage that is not high enough to cause a stage of a motor braking circuit to establish a current path across a load resistor. Once the maximum speed in the first speed range is exceeded, a second speed range 2608 may be entered in which the braking motor 2056 is operated to apply a braking force, by applying a load through a braking circuit. More particularly, the minimum speed of the second speed range 2608 occurs at a rotationally velocity of the braking motor 2056 at which the braking motor 2056 produces a voltage sufficient to trigger application of a load stage or branch of the motor braking circuit. The force applied by the braking motor 2056, and therefore the force required to continue moving the platform initially experiences a step increase, and then increases at an essentially linear rate due to the introduction of the resistive load. In a third speed range 2612, the braking motor 2056 is producing a voltage that is high enough to trigger application of a second load branch, as well as the first load branch. Upon application of the second load branch, the resistance takes a step increase, and then increases with the voltage output by the braking motor at a rate that is greater than the rate of increase when only the first load was active. Where the first and second load branch or branches each add equal resistive loads, the slope of the increase in the force required to continue rotating the braking motor 2056 increases with velocity at approximately twice the previous rate. If a third stage is included in the circuit, a fourth speed range 2616 can be defined. When the fourth range 2616 is entered, another step increase in the force occurs when the third stage load resistor is added, and the resistance then increases at a linear rate that is greater than the rate of increase in the previous range.

When the velocity of the braking motor 2056 is decreasing, the force applied to the drive wheel 2036 by the braking motor 2056 will follow the same curve as when the velocity was increasing if a zener diode or a pair of dividing resistors and a transistor are used as the switching mechanisms. However, where a resistor and an SCR are used as a switching mechanism, the load resistor associated with such a switching mechanism will continue to be applied until the velocity of the braking motor 2056 (and hence its output) is almost zero. For instance, in a three stage braking circuit in which every stage comprises a resistor and an SCR switching mechanism, once the third speed range 2616 is entered, as the velocity of the motor decreases path 2618 will be followed.

In accordance with other embodiments of the present invention, the values of load resistors included in stages of a braking circuit can be selected from a number of different values to provide a selected resistance at the drive wheel 2036. For example, a ganged switch may be used to select from two or more load resistors that are applied at one or more of the speed ranges. In accordance with still other embodiments of the present invention, a switch for selecting a load resistor can be separately provided for selecting the load resistor or resistors that are applied in forward and reverse directions with respect to the platform. User selectable resistance can also be achieved through use of a potentiometer in place of one or more of the provided load resistors, provided the potentiometer has a suitable load rating. An example of the effect of selecting different, higher resistance load resistors applied at different stages of the braking motor circuit is shown in FIG. 26 as plot 2620. As alternative to being user selectable, the load resistors may be selected or (in the case of a potentiometer) tuned by operation of a switch that is not normally user accessible. In addition, it should be appreciated that a braking motor circuit in accordance with embodiments of the present invention may be tuned such that a load resistor is immediately or almost immediately provided with current by the braking motor 2056, which would eliminate or shorten the first range 2604 during which there is no or almost no increase in the resistive force produced by the braking motor 2056 with increased velocity of the platform. Such tuning may be user adjustable. It can be appreciated by one of skill in the art that the motor braking circuitry provides a means for variably controlling a resistance to the braking motor 2056.

In accordance with embodiments of the present invention, the weight of platform may be adjustable to provide a larger normal force for allowing more braking and/or stopping force to be effectively applied when the brake assembly 1904 and/or drag wheel assembly 1908 are engaged. For example, additional ballast (sand filled articles, weights, etc.) may be located on the support platform 100, 100', 100" to increase the weight of the support platform 100, 100', 100".

It is noted that the transmission system 1500 and/or the rotation resistance mechanism 2052 have application to a variety of platforms and/or mobile devices. For example, a walker may be adapted to incorporate one or more of the transmission system 1500 and the rotation resistance mechanism 2052. As other possible examples of alternative uses, a wheel chair, a baby stroller, a beverage platform for airlines, and/or a serving platform for cruise ships may incorporate these systems, and such applications and others are within the scope of the present invention.

Figure 27:
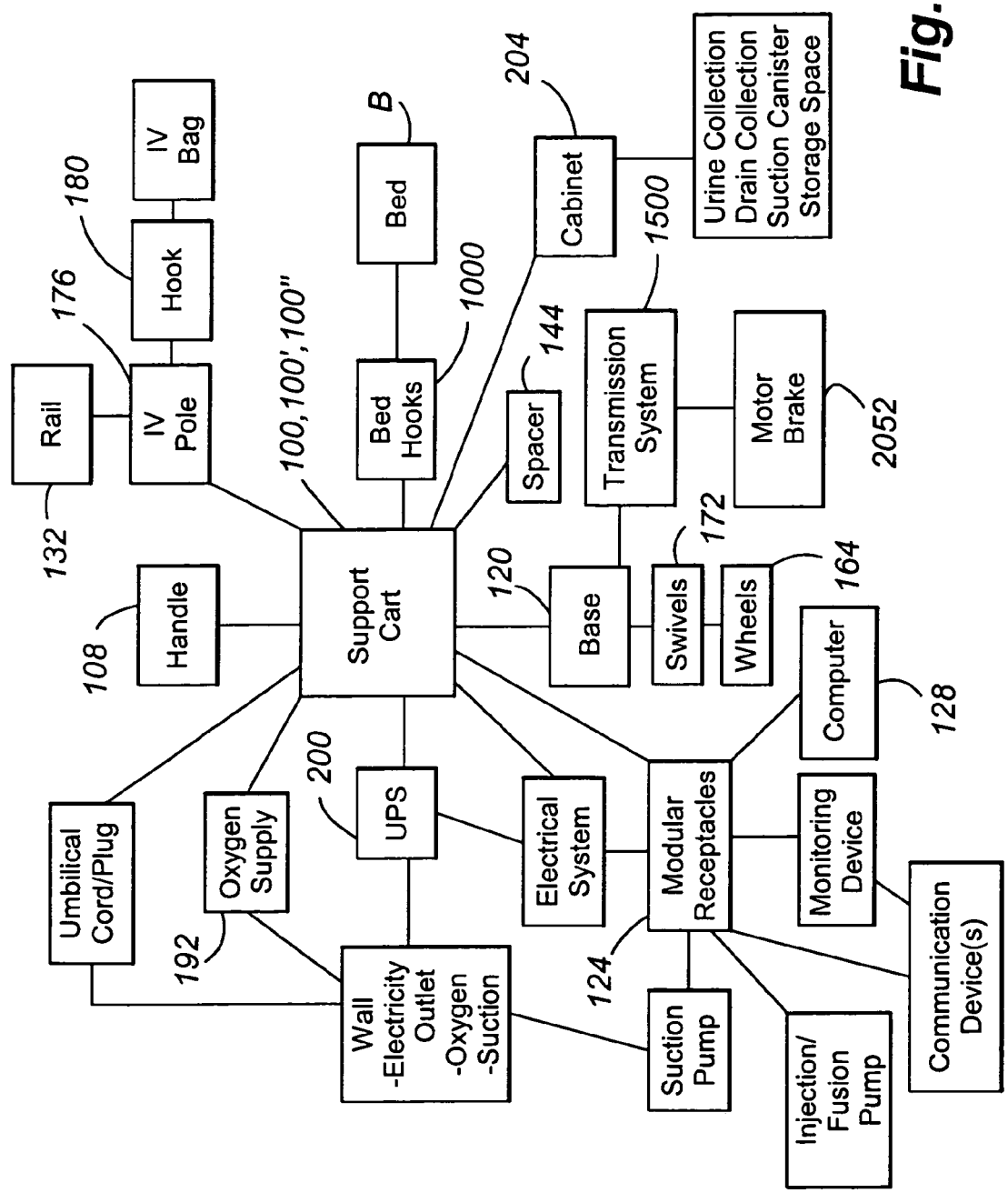
FIG. 27 is a schematic depiction of components that may be included in embodiments of the present invention.

Referring now to FIG. 27, a block diagram or schematic depiction of some of the possible components of the support platform 100, 100', 100" are illustrated. Additional components other than those shown in FIG. 27 are also within the scope of the present invention, including other components described herein, as well as additional items such as a built-in folding seat or a shade canopy/umbrella.

In use, the support platform 100, 100', 100" is initially positioned near the patient's bed. The support platform 100, 100', 100" can be then be modified to meet the patient's needs, such as by adding an IV bag, suction pump, injection pump, and/or oxygen supply, and by adding one or more devices to monitor the vital signs of the patient. By plugging the UPS 200 into an electrical outlet, such as a wall outlet, power can be supplied directly to the support platform, and therefore, power is supplied to items interconnected to the electrical system of the platform. In addition, if available and prescribed, oxygen can be directly supplied to the patient by connecting a stationary oxygen supply to the platform. The platform may also be secured to the patient's bed by utilizing bed hooks 1000 mounted on the support platform 100, 100', 100" to clamp the platform to the framing of the patient's bed.

When the patient is required to be moved from the room while in bed, the support platform can be disengaged from the provided stationary connections by unplugging or otherwise disengaging the connections to the platform, and then subsequently moving the support platform 100, 100', 100" while moving the patient's bed. If the support platform is interconnected to the bed, such as by bed hooks 1000, a separate attendant or nurse may not be needed to move the support platform 100, 100', 100" while moving the bed.

As the patient becomes mobile, the support platform can be used as a walking aid by disengaging the support platform systems from the stationary supply sources, such as electrical power or oxygen. By grasping the handle with one or two hands and pushing the platform, the patient can move away from the bed while IV fluids, pumps, and monitoring equipment on the support platform maintain treatment to the patient.

As can be appreciated by one of skill in the art after consideration of the present disclosure, embodiments of the present invention may provide physiological support to a patient that might not otherwise be conveniently available. For example, in connection with hospitals or clinics in underdeveloped areas, a support platform 100, 100', 100" in accordance with the present invention may provide an integrated package for supplying a patient with oxygen, fluids, suction, waste receptacles, monitoring devices, and electrical power. Furthermore, a support platform 100, 100', 100" in accordance with embodiments of the present invention provides an integrated structure from which such physiological support can be supplied. As can also be appreciated from the description provided herein, the particular features or modules included as part of a support platform 100, 100', 100" in accordance with embodiments of the present invention can be selected according to the particular needs of a patient and can be changed as the needs of the patient change.

In summary, the present invention provides a stable apparatus for assisting a patient walking. Nurses will be able to make better use of their time in the direct care of patients. Patients may have decreased hospital stays, complication rates and less time in skilled-nursing facilities. Fewer therapeutic errors will result and nurses will be at decreased risk for back injuries. The apparatus may include an IV fluids assembly, while also optionally providing modular receptacles for receiving a pump, and further providing an optional uninterruptible power supply for powering one or more electronic devices, such as a pump or one or more pieces of monitoring equipment. The support platform preferably includes adjustable components, including an adjustable handle. The support platform also preferably includes an expandable configuration, such that while the platform may initially be used for simply holding an IV bag, it can be quickly modified to incorporate other prescribed treatments, such as an oxygen supply or injection pump. As the patient progresses through treatment, the support platform transitions from a bedside equipment station and emergency power supply, to a walking aid and wireless communications apparatus.

In accordance with the embodiments of the invention, the platform comprises a ruggedized version that enables the platform to be used in conditions outside of the confines of a healthcare facility. This may include conditions such as military field operations, on-site disasters and underdeveloped regions. The basic premise of the platform is described above, with one or more of the following modifications:

1) larger wheels between the diameters of 6 to 12 inches to traverse rough terrain;

2) a raised base in order to provide greater ground clearance;

3) a broadened base width in order to provide greater stability on unlevel terrain; and 4) the materials may be altered in order to have greater impact tolerance and protection in extreme environments such as high dust, extreme temperatures, air drops, high humidity and inclement weather.

In accordance with still other embodiments of the invention, the platform can be adapted for use in the operating suite environment. Devices such as a headlamp, cautery device, sequential compression device, suction, laparoscopy equipment and gasses may be incorporated onto the platform. This places all of these devices on a single platform both in their current form and in future forms that are designed to fit in as modules that would reduce the overall size and weight of the device. A UPS would again be provided to power the devices and allow the batteries to be removed from each of the individual devices. This would be of benefit both in current OR's and in conditions such as military field conditions or less-developed regions where a self-contained platform would simplify the equipment and reduce the overall bulk. Each platform would be able to be individually configured to meet the specific needs to the user. The user would be able to easily swap modules at the site of use to change the configuration as well.

In accordance with yet another embodiment of the invention, a platform is provided for use in veterinary medicine. One variation comprises a platform for use in small-animal veterinary medicine that is designed for indoor use with modules specific for the care of smaller animals. A second variation comprises a platform for use with larger animals that is more akin to the ruggedized version described above to address the specific concerns of large-animal veterinary medicine.

In accordance with still other embodiments of the present invention, non-medical applications of the device are within the scope of this invention. Brief descriptions of some of the variations are provided. This is not limiting in nature and other variations which utilize the common core of the platform with modifications of the functions and modules provided are intended to be included in the scope of this invention. Several features may be considered common in the platform design or may be found in several variations. The cosmetic appearance of the platform is flexible and appealing including the ability for the user to select color. The small form factor of the invention is maintained and it is to be portable and remain unobtrusive in the environment of use. The device may be modified in order to be moved up and down stairs by a single user without damage to the platform or stairs. A motorized wheel or wheels may be added to aid in the motion of the invention for certain applications. The invention may be modified to include a stepping stool or mini-ladder that provides a stable system for the user with the brake enabled. Additionally, the invention may be modified to help stabilize a ladder by applying the brake and attaching directly to a taller ladder than provided on the platform. A universal power supply may be provided to power internal and external electrical devices.

A non-medical embodiment of this invention may be for use in a beauty salon. The invention may include a sink with drain, water supply and storage compartments in order to provide a beautician or stylist with all of the elements required to cut, style and wash a client's hair.

A non-medical embodiment of this invention may be for use in pet and animal grooming. The invention may include a sink, drain, grooming surface, hooks and compartments for grooming supplies, food and toys. The device may be expected to be used at professional grooming salons, in showmanship venues and at home.

A non-medical embodiment of this invention may be for use in a garage for auto mechanics. The invention may contain an air compressor, hangar for a light source, tool compartments, hangar for a sleeper platform and compatibility with diagnostic hardware and software. This may include wireless transmission of data to a central diagnostic unit. This would allow a single mechanic or multiple mechanics with similar devices to work autonomously in a garage with their vital equipment readily available at their side.

A non-medical embodiment of this invention may be for use at home or in a handyman shop as a tool caddy. The invention may contain an air compressor, light source, tool compartments, compartments for accessories such as screws and nails, and an attachment to help stabilize a footstool or ladder.

A non-medical embodiment of this invention may be for use in indoor or outdoor landscaping. The wheel base will be modified to indoor or outdoor as similarly described previously for the medical aspect of this invention. The invention may also include a pressurized liquid tank or tanks for water, pesticides or fertilizers. Additional features may include a debris bin and storage bins for tools.

A non-medical embodiment of this invention may be for use in building maintenance. The invention may include a power supply, air compressor, compressed fluid storage, diagnostic equipment, wireless transmission capability, computer integration, tool compartments, attachments for spools of wire or tubing, a work stool and the ability to stabilize a ladder by enabling the brake and attaching to a ladder. It may also have a built in stepping stool or mini-ladder.

A non-medical embodiment of this invention may be for use by the elderly or handicapped in order to become more independent in or outside of the home. The stability of the structure will provide the user an aide in ambulation. Additionally, the invention will provide support, unlike current ambulatory aide devices, such as oxygen, compartments to hold drainage bags, cellular/wireless support to provide emergency aide, compartments to hold supplies, personals and groceries or other personal goods, a resting stool and an umbrella. Aide devices as in the medical version of the platform will be used for persons with disabilities such as amputations, paralysis or other chronic conditions to allow them to use the platform effectively. A connector or system, such as the one previously developed to connect the invention to a hospital bed, may be developed to connect to a trailer hitch for easy transport with a vehicle. A portion or portions of the invention may easily detach for transfer of the module to a vehicle or residence without requiring transfer of the entire platform. The hope with this embodiment is to mobilize and reintroduce persons into society that were previously confined or restricted secondary to their disabilities.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. A personal support platform for traversing an underlying surface, comprising:

a frame;

a plurality of caster wheels interconnected to said frame;
a drag wheel interconnected to the frame and moveable between a raised position and a lowered position;
a braking assembly interconnected to the frame having an engaged and a disengaged position, wherein in the engaged position the braking assembly causes a frictional force to be applied to the underlying surface sufficient to prevent translational movement of the personal support platform, the frictional force not being applied through the drag wheel;
a transmission system interconnected to said frame, said transmission system providing a number of user selectable modes, said user selectable modes comprising at least a stop mode, a walk mode and a roll mode, wherein in the stop mode the drag wheel is lowered and the braking assembly is engaged, in the walk mode the drag wheel is lowered and the braking assembly is disengaged, and in roll mode the drag wheel is raised and the braking assembly is disengaged; and
a single selector mechanism for selectively choosing one of said stop, walk and roll modes by a user from a standing position adjacent said frame.

2. The platform as claimed in claim 1, wherein said transmission system comprises a cam interconnected to said frame and the drag wheel, wherein said cam is rotatably movable to raise and lower said drag wheel from said raised position in said roll mode to said lowered position in said walk mode.

3. The platform as claimed in claim 2, further comprising an automatic brake interconnected to said drag wheel, said automatic brake comprising a braking motor driven by said drag wheel and circuitry, wherein said circuitry provides a resistive load to the braking motor to apply a braking force on the drag wheel.

4. The platform as claimed in claim 3, wherein said resistive load comprises a number of load ranges, wherein a first load range provides a first resistive load within a first velocity range for said braking motor, and wherein a second load range provides a second resistive load within a second velocity range for said braking motor.

5. The platform as claimed in claim 4, wherein said second velocity range is automatically selected once a threshold velocity of said braking motor is reached.

6. The platform as claimed in claim 1, wherein said braking assembly is selectively moveable from a first raised position in said walk and roll modes to a second lowered position in said stop mode, wherein said braking assembly is for contacting the underlying surface when in said second position.

7. The platform as claimed in claim 6, wherein said braking assembly comprises a stopper frictionally engaging the underlying surface.

8. The platform as claimed in claim 6, further comprising a cam having a first channel interconnected to said braking assembly.

9. The platform as claimed in claim 8, wherein said cam comprises a second channel interconnected to the drag wheel.

10. The platform as claimed in claim 9, wherein first channel comprises a first ramp for raising and lowering a first post interconnecting said drag wheel to said cam, and wherein said second channel comprises a second ramp for raising and lowering a second post interconnecting said stopper to said cam.

11. The platform as claimed in claim 1, wherein said single selector mechanism comprises a rotatable control bar having a first handle at a rear portion of said frame, said handle selectively adjusting a setting of said transmission system.

12. The platform as claimed in claim 11, wherein the rotatable control bar further comprises a second handle at a front portion of said frame, said second handle selectively adjusting a setting of said transmission system.

13. The platform as claimed in claim 1, further comprising at least one grasping mechanism for interconnecting said frame to another structure.

14. The platform as claimed in claim 13, wherein said grasping mechanism comprises a rotatable gripper arm that engages the other structure.

15. The platform as claimed in claim 14, wherein said rotatable gripper arm rotates about a first axis in a direction away from said frame, and rotates about a second axis to grasp the other structure, wherein said second axis is transverse to said first axis.

16. A personal support platform for traversing an underlying surface, comprising:
a frame;
means for rotating interconnected to said frame and contacting the underlying surface;
means for frictionally engaging the underlying surface and interconnected to said frame; and
means for variably controlling a resistance provided by said means for frictionally engaging, comprising a passive braking motor including:
a motor braking circuit interconnected to the passive braking motor, including:
a first circuit stage, including:
a switching mechanism, wherein an activation voltage for the first circuit stage is defined;
a load resistor, wherein when the passive braking motor produces an amount of power sufficient to produce a voltage at the switching mechanism that is equal to or greater than the activation voltage a current is allowed to pass through the load resistor.

17. The platform as claimed in claim 16, wherein said means for rotating comprises a plurality of caster wheels.

18. The platform as claimed in claim 16, wherein said means for frictionally engaging comprises a drag wheel.

19. The platform as claimed in claim 16, wherein said means for frictionally engaging is interconnected to a means for adjusting a position of said means for frictionally engaging, wherein said means for adjusting may alter a position of said means for frictionally engaging from a first position in contact with the underlying surface to second position wherein said means for frictionally engaging does not contact the underlying surface.

20. The platform as claimed in claim 19, wherein said means for adjusting comprises a selectably positionable cam for raising and lowering said means for frictionally engaging.

21. A personal support platform for traversing an underlying surface, comprising:
a frame;
a plurality of caster wheels interconnected to the frame;
a drag wheel interconnected to the frame; and
a passive braking motor connected to and driven by the drag wheel including:
a motor braking circuit interconnected to the passive braking motor, including:
a first circuit stage, including:
a switching mechanism, wherein an activation voltage for the first circuit stage is defined;
a load resistor, wherein when the passive braking motor produces an amount of power sufficient to produce a voltage at the switching mechanism that is equal to or greater than the activation voltage a current is allowed to pass through the load resistor.

22. The platform as claimed in claim 21, further comprising:
a braking assembly interconnected to the frame having an engaged and a disengaged position, wherein in the engaged position the braking assembly causes a frictional force to be applied to the underlying surface sufficient to prevent translational movement of the personal support platform, the frictional force not being applied through the drag wheel.

23. The platform as claimed in claim 22, further comprising:
a transmission system interconnected to said frame, said transmission system providing a number of user selectable modes, said user selectable modes comprising at least a stop mode, a walk mode and a roll mode, wherein in the stop mode the drag wheel is lowered and the braking assembly is engaged, in the walk mode the drag wheel is lowered and the braking assembly is disengaged, and in roll mode the drag wheel is raised and the braking assembly is disengaged.

24. The platform as claimed in claim 23, further comprising:
a single selector mechanism for selectively choosing one of said stop, walk and roll modes by a user from a standing position adjacent said frame.

25. The platform as claimed in claim 24, wherein said single selector mechanism comprises a rotatable control bar having a first handle at a rear portion of said frame, said handle selectively adjusting a setting of said transmission system.

26. The platform as claimed in claim 25, wherein the rotatable control bar further comprises a second handle at a front portion of said frame, said second handle selectively adjusting a setting of said transmission system.

27. The platform as claimed in claim 23, wherein said braking assembly is selectively moveable from a first raised position in said walk and roll modes to a second lowered position in said stop mode, wherein said braking assembly is for contacting the underlying surface when in said second position.

28. The platform as claimed in claim 27, wherein said braking assembly comprises a stopper frictionally engaging the underlying surface.

29. The platform as claimed in claim 28, further comprising a cam having a first channel interconnected to said braking assembly.

30. The platform as claimed in claim 29, wherein said cam comprises a second channel interconnected to the drag wheel.

* * * * *